United States Patent
Jois et al.

(10) Patent No.: US 9,963,486 B2
(45) Date of Patent: May 8, 2018

(54) PEPTIDOMIMETICS FOR TREATING HER2-OVEREXPRESSED CANCER

(71) Applicants: Seetharama D. Jois, West Monroe, LA (US); Shanthi Kanthala, Monroe, LA (US)

(72) Inventors: Seetharama D. Jois, West Monroe, LA (US); Shanthi Kanthala, Monroe, LA (US)

(73) Assignee: Board of Supervisors for the University of Louisiana System, Monroe, LA (US)

( * ) Notice: Subject to any disclaimer, the term of this patent is extended or adjusted under 35 U.S.C. 154(b) by 0 days. days.

(21) Appl. No.: 15/310,238

(22) PCT Filed: May 7, 2015

(86) PCT No.: PCT/US2015/029606
§ 371 (c)(1),
(2) Date: Nov. 10, 2016

(87) PCT Pub. No.: WO2015/175299
PCT Pub. Date: Nov. 19, 2015

(65) Prior Publication Data
US 2017/0267725 A1 Sep. 21, 2017

Related U.S. Application Data

(60) Provisional application No. 61/991,834, filed on May 12, 2014.

(51) Int. Cl.
*A61K 38/03* (2006.01)
*C07K 7/64* (2006.01)
*A61K 38/00* (2006.01)

(52) U.S. Cl.
CPC ............... *C07K 7/64* (2013.01); *A61K 38/03* (2013.01); *A61K 38/00* (2013.01)

(58) Field of Classification Search
None
See application file for complete search history.

(56) References Cited

PUBLICATIONS

Satyanarayanajois, S. et al., "Design, Synthesis, and Docking Studies of Peptidomimetics Based on HER2-Herceptin Binding Site with Potential Antiproliferative Activity Against Breast Cancer Cell Lines," Chem. Biol. Drug Des., vol. 74, No. 3, pp. 246-257 (2009).
Badache, A. et al., "A New Therapeutic Antibody Masks ErbB2 to its Partners," Cancer Cell, pp. 299-301 (2004).
Biobusiness Briefs, "ERBB2 Dimerization Inhibitor Meets End Point in Breast Cancer Trial," Nature Drug Discovery, vol. 10, pp. 648 (2011).
Berezov, A. et al., "Disabling ErbB Receptors with Rationally Designed Exocyclic Mimetics of Antibodies: Structure-Function Analysis," J. Med. Chem., vol. 44, pp. 2565-2574 (2001).
Pero, S. etal., "Identification of a Small Peptide that Inhibits the Phosphorylation of ErbB2 and Proliferation of ErbB2 Overexpressing Breast Cancer Cells,"Int. J. Cancer, vol. 111, pp. 951-960 (2004).
Dakappagari, N. et al., "Conformation HER-2/neu B-cell Epitope Peptide Vaccine Designed to Incorporate Two Native Disulfide Bonds Enhances Tumor Cell Bonds Enhances Tumor Cell Binding and Antitumor Activities," J. Biol. Che., vol. 280, pp. 54-63 (2005).
Fasan, R. et al., "Structure-Activity Studies in a Family of β-Hairpin Protein Epitope Mimetic Inhibitors of the p53-HDM2 Protein-Protein Interaction," ChemBioChem, vol. 7, pp. 515-526 (2006).
Cho, H. et al., "Structure of the Extracellular region of HER2 Alone and in Complex with the Herceptin Fab," Nature, vol. 421, pp. 756-760 (2003).
Banappagari, S. et al., "A Conformationally Constrained Peptidomimetic Binds to the Extracellular Region of HER2 Protein," J. Biomol. Struc. vol. 28, No. 3, pp. 1-20 (2010).
Banappagari, S. et al., "Structure-Activity Relationship of Conformationally Constrained Peptidomimetics for Antiproliferative Activity in HER2-Overexpressing Breast Cancer Cell Lines," Med. Chem. Commun., vol. 2, pp. 752-759 (2011).
Banappagari, S. et al., "Inhibition of Protein-Protein Interacation of HER2-EGFR and HER2-HER3 by a Rationally Designed Peptidomimetic," J. Biomol. Struct. Dyn. vol. 30, pp. 594-606 (2012).
Banappagari, S. et al., "Design, Synthesis and Characterization of Peptidomimetic Conjugate of BODIPY Targeting HER2 Protein Extracellular Domain," Eur. J. Med. Chem., vol. 65C, pp. 60-69 (2013).
Gokhale, A. et al., " Conformationally Constrained Peptides from CD2 to Modulate Protein-Protein Interactions Between CD2 and CD58," J. Med. Chem., vol. 54, No. 15, pp. 5307-5319 (2011).
Muhamad, A. et al., Solution Structure and in Silico Binding of a Cyclic Peptide with Hepatitis B Surface Antigen, Chen Biol Drug Des., vol. 81, pp. 784-794 (2013).
Kanthala, S. et al., "Structure-Activity Relationships of Peptidomimetics That Inhibit PPI of HER2-HER3," Biopolymers, vol. 101, No. 6, pp. 693-702 (2014).
Kanthala, S. et al., "Novel Peptidomimetics for Inhibition of HER2:HER3 Heterodimerization in HER2-Positive Breast Cancer," Che. Biol. Drug Des., doi: 10.1111/cbdd.12453 (2014).

*Primary Examiner* — Lianko G Garyu
*Assistant Examiner* — Khalid Kader
(74) *Attorney, Agent, or Firm* — John H. Runnels

(57) ABSTRACT

Novel peptidomimetic compounds are disclosed, compounds that inhibit protein-protein interactions (PPI) of epidermal growth factor receptors (EGFR), also called human epidermal growth factor receptors (HERs), and that block signaling for cell growth in HER2-overexpressed cancers. The novel peptidomimetics specifically bind the HER2 protein, and thereby inhibit dimerization. The peptidomimetics disrupt both HER2-HER3 and EGFR-HER2 heterodimer formation. The peptidomimetics can be used in the treatment of various types of HER2-overexpressed cancers, including lung, breast, and ovarian cancers.

10 Claims, 21 Drawing Sheets

X=CH₃, Cl, F, Br, H

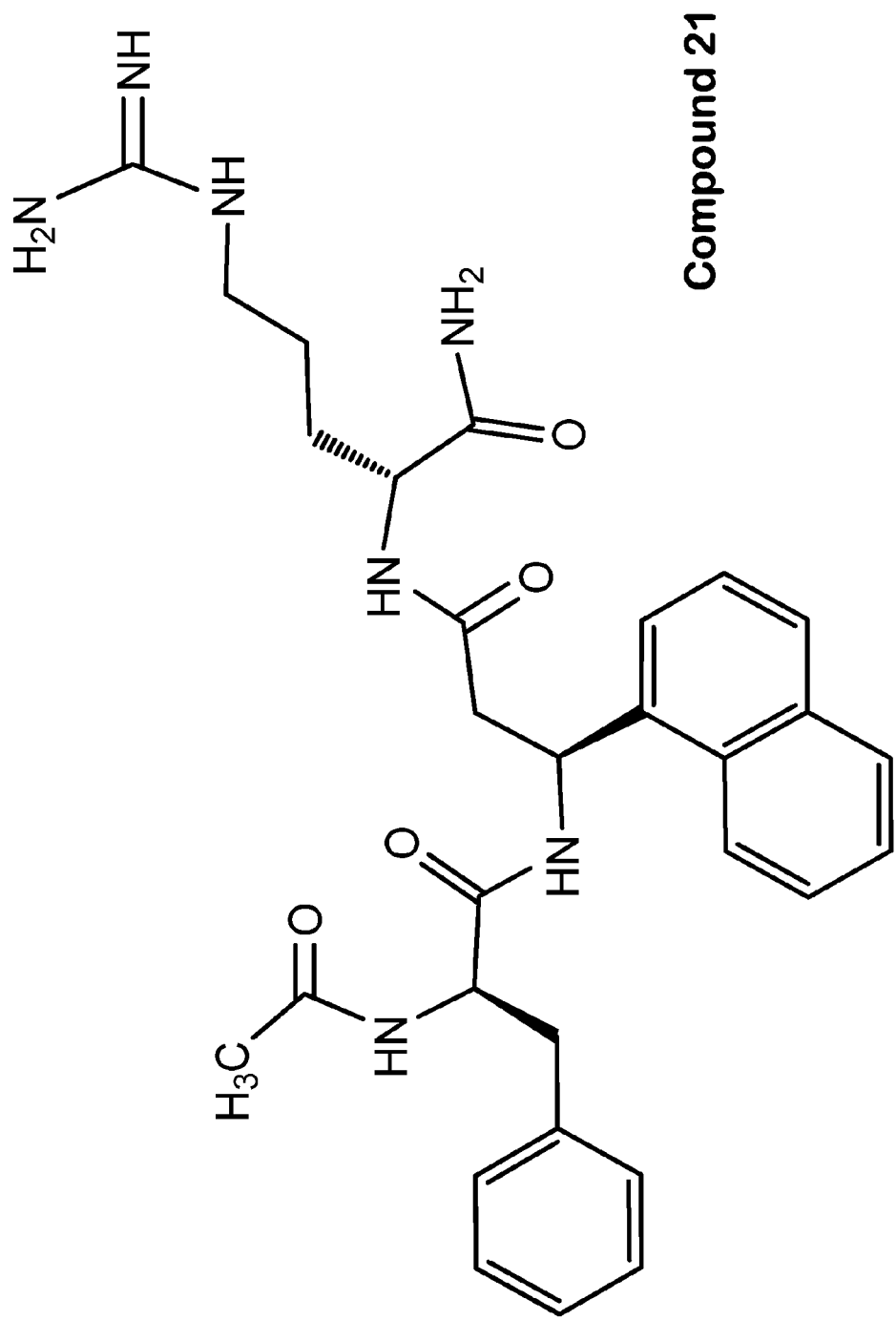
Fig. 12 Compound 21

PEPTIDOMIMETICS FOR TREATING HER2-OVEREXPRESSED CANCER

This is the United States national stage of international application PCT/US2015/029606, international filing date May 7, 2015, which claims the benefit of the May 12, 2014 filing date of U.S. provisional patent application Ser. No. 61/991,834 under 35 U.S.C. § 119(e).

This invention was made with Government support under grant number 8P20GM103424 awarded by the National Institutes of Health. The United States Government has certain rights in the invention.

TECHNICAL FIELD

This invention pertains to peptidomimetics and methods for using peptidomimetics to treat HER2-overexpressed cancers.

BACKGROUND ART

Epidermal growth factor receptors (EGFRs) are highly expressed in many human cancers. Four EGFRs have been reported: EGFR, HER2, HER3, and HER4. Three of these, EGFR, HER2, and HER3, have been implicated in cancers, especially in aggressive lung, breast, and ovarian cancers.

EGFRs belong to the transmembrane receptor tyrosine kinase family of receptors that mediate cell signaling and influence cell growth, differentiation, and motility. These receptors are activated by ligands that change the conformation of the extracellular domains. Ligand binding induces receptor dimerization and activation of intracellular tyrosine kinase activity, which in turn leads to downstream signaling pathways. In normal cells, following activation of the initial signal transduction mechanism, receptor activation is attenuated by mechanisms such as receptor internalization and down-regulation. However, aberrant EGFR signaling occurs in certain cancers. Signal dysregulations due to receptor mutation, constitutive activation, overexpression of receptors, and dimerization have been reported in several types of cancers.

Non-small-cell lung cancer is the most common type of lung cancer. It is a leading cause of cancer deaths worldwide. In approximately 18-33% of non-small-cell lung cancer tumors human epidermal growth factor receptor-2 (HER2) is overexpressed. The prognosis of patients with lung cancer is poor, with a typical survival rate around one year. The coexpression of EGFR and HER2 is associated with an even lower survival rate. HER2 is also overexpressed in 20-30% of invasive breast cancers. HER2:HER3 dimers, and the interaction of HER2 with HER3 and EGFR are known to be important in HER2-overexpressing breast tumors.

Existing approaches to cancer therapy include chemotherapeutic agents, hormonal therapy, antibodies targeted to the HER2 protein, and tyrosine kinase inhibitors. Amplification of the HER2 gene is associated with poor prognosis and resistance to certain chemotherapeutic agents. Hormonal therapy is not an option for HER2-positive cancers. Antibodies and tyrosine kinase inhibitors have shown some positive responses in treating such types of cancers. However, there are limitations to the stability and immunogenicity of antibodies. There are more than 500 different kinases in the body that can be affected by tyrosine kinase inhibitors. Resistance to tyrosine kinase inhibitors typically develops within a few years.

Satyanarayanajois S, Villalba S, Jianchao L, Lin G M. (2009). Design, synthesis, and docking studies of peptidomimetics based on HER2-herceptin binding site with potential antiproliferative activity against breast cancer cell lines. *Chem. Biol. Drug Des.* 74: 246-257 discloses the in silico screening of several peptidomimetics for their effect on HER2 binding.

To treat HER2-positive cancers such as breast cancer, the HER2 domain IV has been targeted by an antibody such as trastuzumab, and HER2 domain II has been targeted by an antibody such as pertuzumab. See A. Badache and N. Hynes, A new therapeutic antibody masks ErbB2 to its partners, *Cancer Cell*, April 2004, 299-301; and Biobusiness Briefs, ERBB2 dimerization inhibitor meets end point in breast cancer trial, *Nature Drug Discovery*, vol. 10, September 2011, 648.

Peptides targeting HER2 are disclosed in A. Berezov et al., Disabling ErbB Receptors with Rationally Designed Exocyclic Mimetics of Antibodies: Structure-Function Analysis, *J. Med. Chem.* 2001, 44, 2565-2574; S. Pero et al., Identification of a small peptide that inhibits the phosphorylation of ErbB2 and proliferation of ErbB2 overexpressing breast cancer cells, *Int. J. Cancer:* 111, 951-960 (2004); A Berezov et al., Disabling ErbB receptors with rationally designed exocyclic mimetics of antibodies: structure-function analysis, *J. Med. Chem.* 2001, 44, 2565-2574; and N. Dakappagari et al., Conformation HER-2/neu B-cell epitope peptide vaccine designed to incorporate two native disulfide bonds enhances tumor cell bonds enhances tumor cell binding and antitumor activities, *J. Biol. Chem.:* 280, 54-63 (2005).

R. Fasan et al, Structure-activity studies in a family of β-hairpin protein epitope mimetic inhibitors of the p53-HDM2 protein-protein interaction, *ChemBioChem*, 2006, 7, 515-526 discloses the use of a cyclic peptide incorporating D-Pro and L-Pro to target HDM2-p53 protein interactions.

H. Cho et al., Structure of the extracellular region of HER2 alone and in complex with the Herceptin Fab, *Nature*, 2003, 421, 756-760 describes studies with the antibody trastuzumab suggesting that HER2 is a potential target for anticancer therapies.

S. Banappagari et al., A conformationally constrained peptidomimetic binds to the extracellular region of HER2 protein, *J. Biomol. Struc.:* 28, No. 3, 1-20 (2010) discloses several peptidomimetics designed to inhibit HER2-mediated heterodimerization and signaling. See also S. Banappagari et al., Structure-activity relationship of conformationally constrained peptidomimetics for antiproliferative activity in HER2-overexpressing breast cancer cell lines, *Med. Chem. Commun.*, 2011, 2: 752-759.

Banappagari S, Corti M, Pincus S, Satyanarayanajois S D. (2012). Inhibition of protein-protein interaction of HER2-EGFR and HER2-HER3 by a rationally designed peptidomimetic. *J. Biomol. Struct. Dyn.* 30: 594-606 discloses a peptidomimetic that bound specifically to the HER2 protein extracellular domain and disrupted the dimerization of EGFRs. See also Banappagari, S., McCall, A., Fontenot, K., Vicente, M. G. H., Gujar, A., Satyanarayanajois, S. D. (2013). Design, synthesis and characterization of peptidomimetic conjugate of BODIPY targeting HER2 protein extracellular domain. *Eur J. Med. Chem.* 65C: 60-69.

There is an unfilled need for improved treatments for patients with HER2-overexpressed cancers such as lung, breast, and ovarian cancers.

SUMMARY OF THE INVENTION

We have discovered novel peptidomimetics that inhibit protein-protein interactions (PPI) of epidermal growth factor receptors (EGFR), also called human epidermal growth factor receptors (HERs). The novel compounds block signaling pathways for cell growth in HER2-overexpressed cancers. The novel peptidomimetics specifically bind the HER2 protein, and thereby inhibit its dimerization. The peptidomimetics disrupt the formation of heterodimers such as HER2-HER3 and EGFR-HER2. The peptidomimetics can be used in the treatment of various types of HER2-overexpressed cancers, including lung, breast, and ovarian cancers.

HER2 interacts with other EGFRs and to form dimers or heteromers. HER2-HER3 and EGFR-HER2 heterodimer interactions can influence both normal cell growth and cancer growth. Blocking the interaction between HER2 and other EGFRs with the novel peptidomimetics will help control cell growth and provide therapeutic benefit for cancer patients.

Peptidomimetics have advantages over both antibodies and conventional peptides. Peptidomimetics are generally more stable, they can often be delivered orally, they can be absorbed readily in the intestine, they generally exhibit good pharmacokinetic properties in vivo, and they tend to be more resistant to enzymatic degradation. The novel peptidomimetics bind to domain IV of HER2. They exhibit antiproliferative activity in the lower nanomolar concentration range against HER2-overexpressed cancers including breast, ovarian, and lung cancers. Furthermore, the peptidomimetics inhibit kinase domain phosphorylation. They have successfully suppressed tumors in vivo in a xenograft animal model for breast cancer.

In one embodiment, the peptidomimetics are admixed with compatible compounds or compositions to form consumable products. In another embodiment, the peptidomimetics are admixed with compatible compounds or compositions to form orally ingestible products. In another embodiment, medicaments contain the disclosed peptidomimetics. Also disclosed are methods of manufacturing medicaments, the methods comprising incorporating therein the disclosed peptidomimetics.

Exemplary of the novel peptidomimetics are Compound 18 and its stereoisomers. Compound 18, with its cyclic structure and D-amino acid, was found to be relatively stable in vivo. The solubility of Compound 18 in water was moderate. Because the compound is lipophilic, Compound 18 crosses intestinal barriers, meaning that it can be administered orally.

Exemplary Compound 18 targets the extracellular domain IV of HER2 to disrupt protein-protein interactions. Compound 18 includes functional groups Arg-[3-amino-3-(1-napthyl propionic acid)]-Phe-Asp, which binds to HER2. For brevity, the 3-amino-3-(1-napthyl propionic acid) moiety will sometimes be called "Anapa." Two D-prolines may be used alone in Compound 18, or one D-proline and one L-proline, and possibly even two L-prolines. The Arg, Phe, and Asp amino acids may be independently in D- or L-conformation.

Two earlier compositions that we had tested, Compounds 5 and 9, had a linear structure, which left N- and C-termini accessible for enzymatic degradation by amino- and carboxy-peptidases. By contrast, Compound 18 has a cyclic structure which incorporates a D-amino acid (D-proline). These features increase stability against enzymatic degradation in vivo. Compound 21 (depicted in FIG. 12) is an analog of Compound 5, having D-amino acids and a reversed sequence as compared to compound 5. The N- and C-termini in compound are acetylated and amidated to protect against degradation.

Compounds 5 and 9 degraded in mouse serum experiments with an in vivo half-life of about 2 to 3 hours. In similar experiments, Compound 18 had a half-life of over 48 hours. In addition, Compound 18 has shown higher potency against HER2-expressing lung cancer cells and greater antiproliferative activity as compared to Compound 5 or Compound 9.

By introducing the same (or similar) functional groups on both ends of the peptidomimetic, the binding affinity of the peptidomimetic to the HER2 protein is enhanced. To join the two binding sites, we introduced conformational constraints in the peptidomimetic sequence using both D-Pro and L-Pro. The peptide was cyclized to enhance stability against enzymatic degradation, forming Compound 18.

Compound 18 binds specifically to HER2 protein extracellular domain IV. Compound 18 inhibits the formation of both HER2:HER3 and EGFR:HER2 heterodimers. Such dual inhibitor activity provides advantages in treating HER2-overexpressed cancers.

BRIEF DESCRIPTION OF THE DRAWINGS

FIG. 12 depicts the structure of Compound 21.

MODES FOR CARRYING OUT THE INVENTION

Figure 1A:
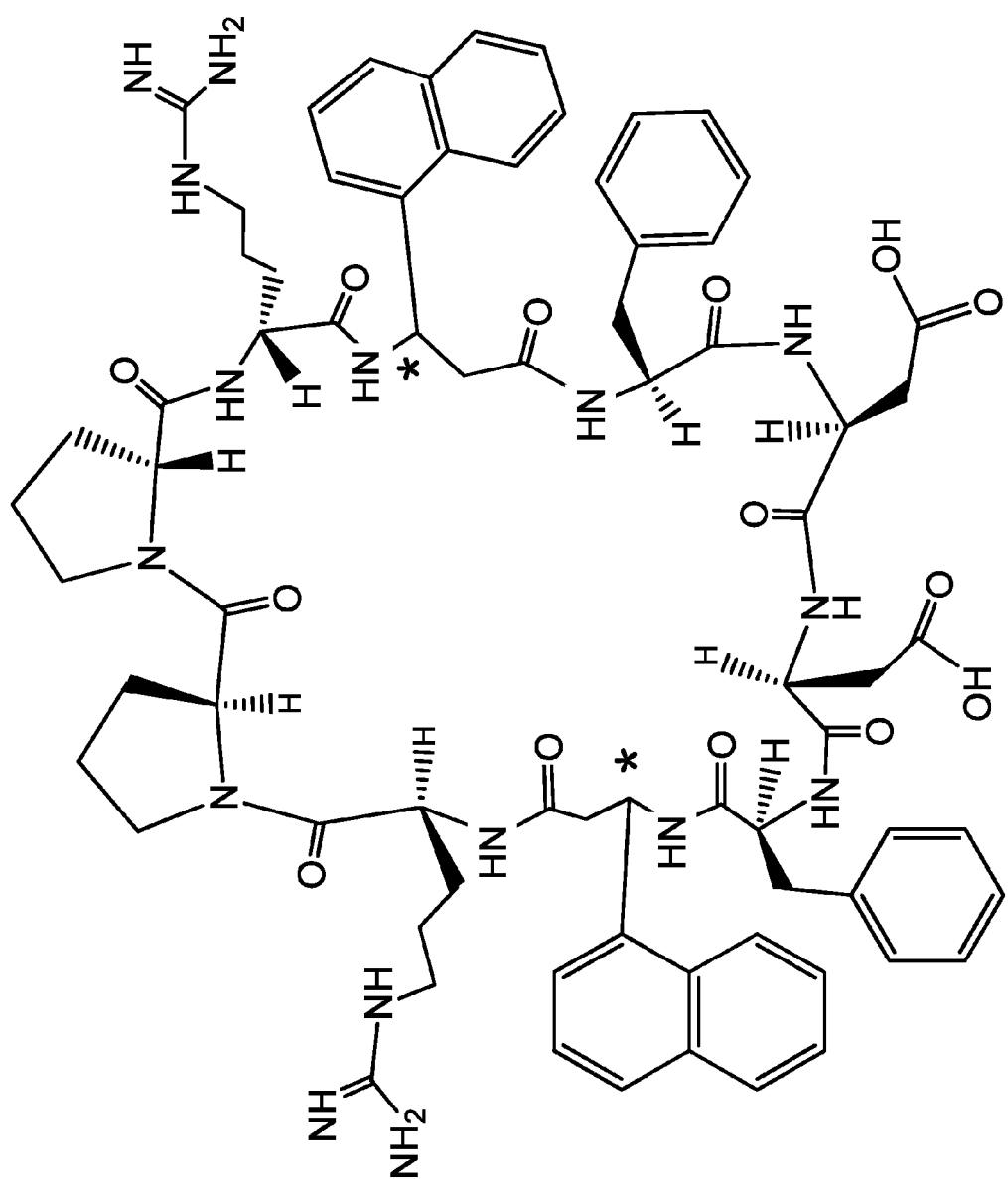
FIG. 1A depicts the structure of Compound 18. Either the left side or the right side of the molecule can bind to the HER2 receptor. At least one side of the molecule has a D-proline. Optionally, both sides have D-prolines. Preferably, with L-Pro-D-Pro, the Anapa has R configuration; and with D-Pro-L-Pro, the Anapa has the S configuration. We have not yet tested D-Pro-D-Pro, but expect that it will also show activity.
Figure 1B:
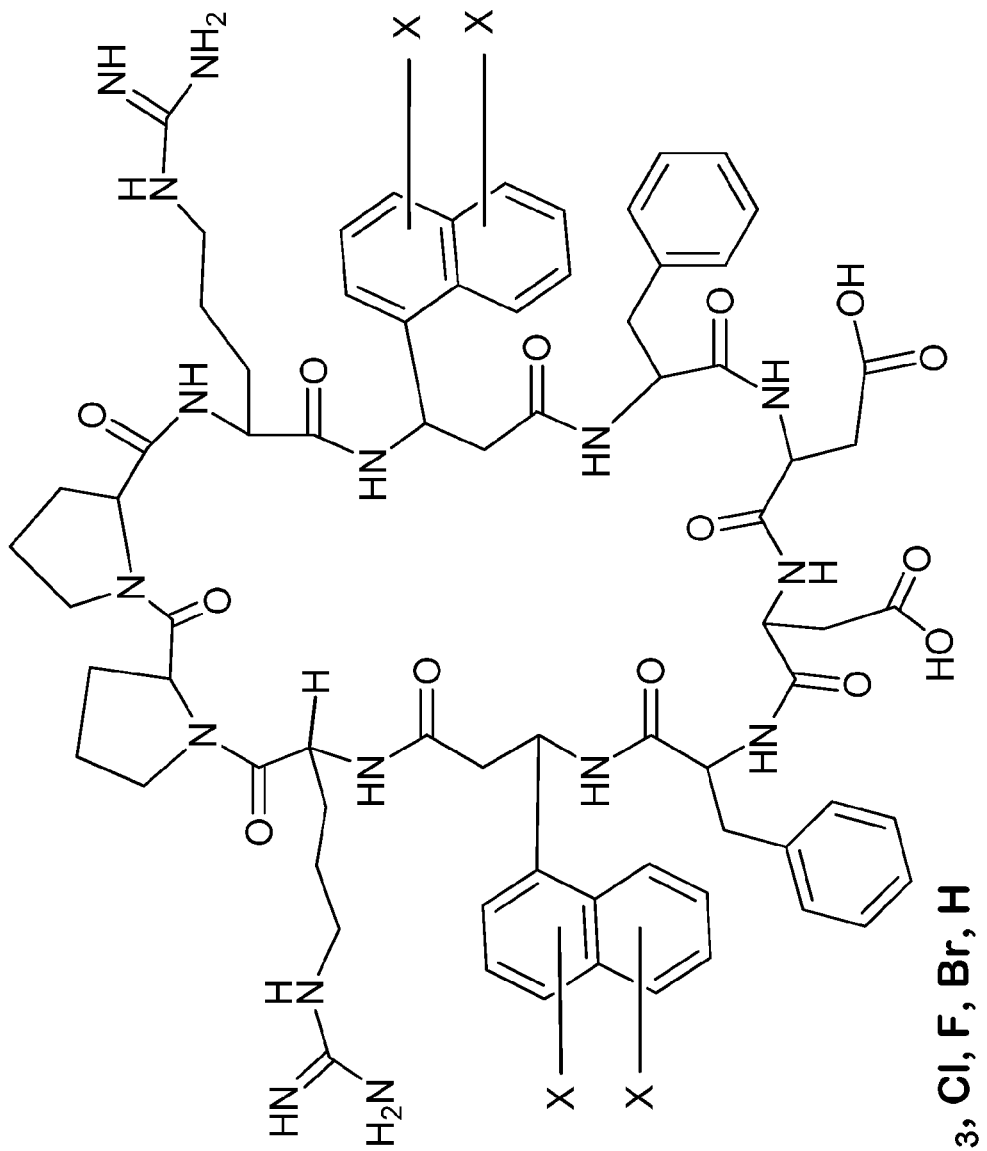
FIG. 1B depicts a generalization of the structure of Compound 18, other compounds that may also be used in practicing this invention.

The structure of Compound 18 is shown in FIG. 1A, and a generalization of that structure is shown in FIG. 1B. Compound 18 can interact with domain IV of HER2 via the pharmacophore on either side of the cyclic structure. Compound 18 can inhibit protein-protein interaction (PPI) between HER2 and other EGFRs. The two instances of the Anapa β-amino acid (*) can independently have an (R) or (S) configuration, resulting in at least four possible stereoisomers of Compound 18 from the Anapa moieties alone: (R,S), (S,R), (R,R), and (S,S).

Likewise, each of the several amino acid residues in Compound 18 or its generalizations can independently have a D- or an L-configuration. As illustrated in FIG. 1B, the Anapa naphthyl group can optionally be substituted with one or two Xs, where each X is independently selected from H, $CH_3$, Cl, F, and Br; and each X may be independently selected to be in the 2, 3, 4, 5, 6, 7, or 8 position of the respective naphthyl group (taking the 1 position of the naphthyl group as that which is bonded to the backbone of the compound.)

Figure 1C:
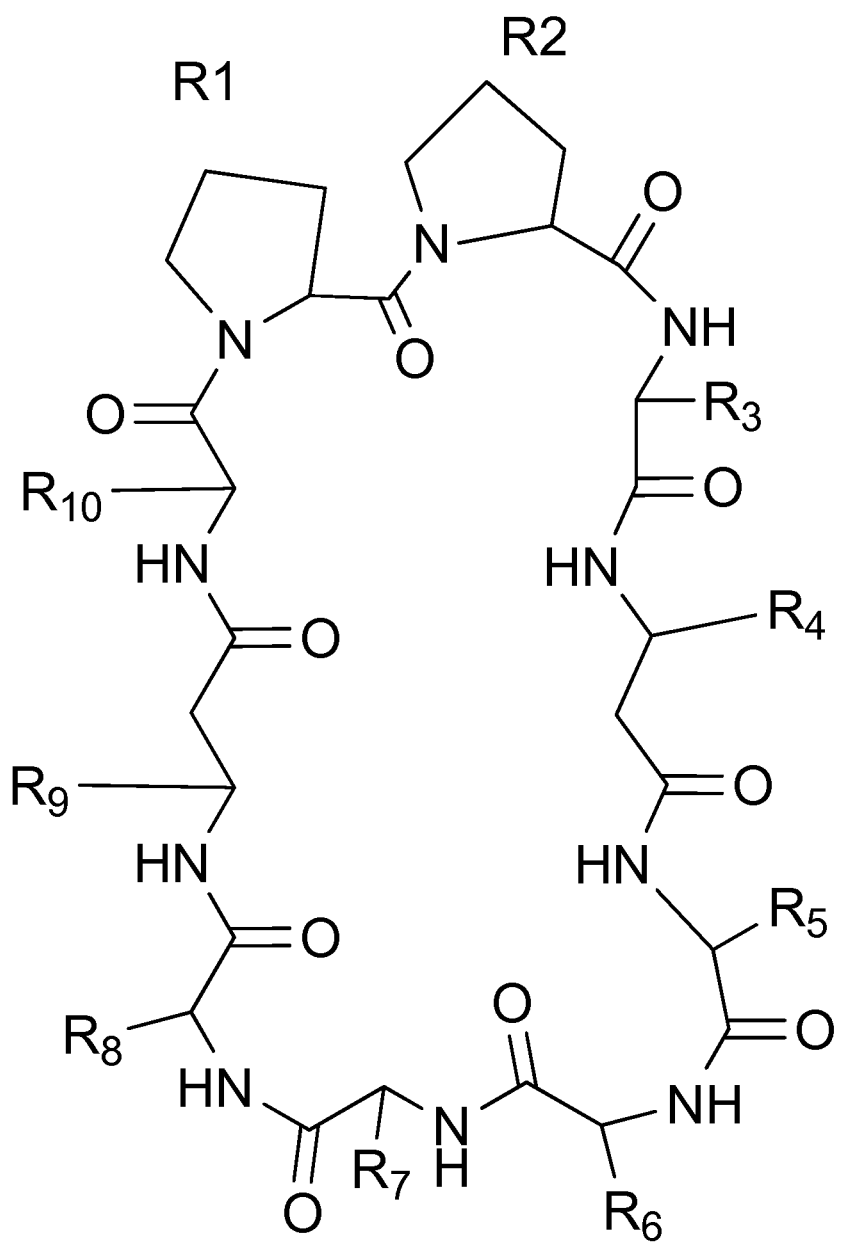
FIG. 1C depicts additional compounds within the scope of the invention.
Figure 1D:
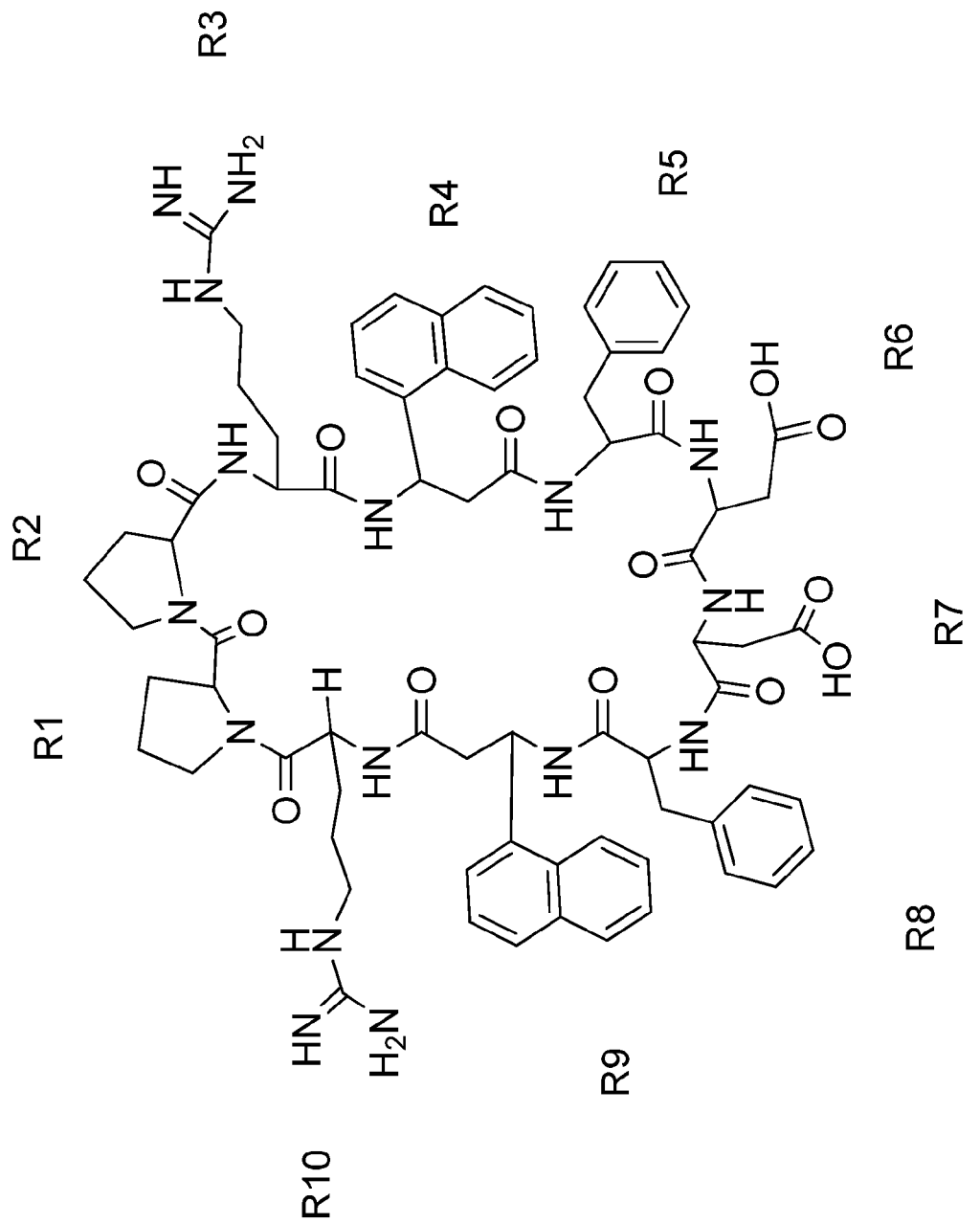
FIG. 1D depicts additional compounds within the scope of the invention.

Additional compounds within the scope of the invention are shown in FIGS. 1C and 1D. Amino acids or beta-amino acid Anapa can optionally be replaced by amino acid analogs as described herein. Additionally, any of the amino acids can have the D or L configuration, and any amino acid analogs can have the R or S configuration.

The structures shown in FIGS. 1C and 1D show moieties, such as R1 and R2, depicted in proximity to a ring structure, but not bonded to a particular carbon atom or heteroatom. In these cases, the moiety may be bonded to any atom within the ring, where permitted by ordinary considerations of valence, oxidation state, and steric constraints.

Exemplary but not limiting substituents, aside from those implicit in the structure of Compound 18 itself, include the following: R3 and R10 may optionally be arginine or analogs of arginine. R4 and R9 may optionally be a hydrophobic group with a fused ring system, tryptophan, tryptophan analogs, naphthyl, or substituted naphthyl. R5 and R8 may optionally be phenyl or substituted phenyl. R6 and R7 may optionally be aspartic acid, aspartic acid analogs, glutamic acid, or glutamic acid analogs. Each substituent may be selected independently; for example, R3 and R10 may be the same or different.

By way of example, non-limiting possibilities for the various substituents include the following: R3 and R10 may optionally be 2-amino-3-guanidinopropionic acid, or Arg (Me). R4 and R9 may optionally be 6-chloro-D-tryptophan, (2S,3aS,7aS)-Octahydro-1H-indole, (S)-7-Azatryptopha, 7-benzyloxy-DL-tryptophan, or 3,3-diphenylalanine. R5 and R9 may optionally be 2,4-dichloro-L-phenylalanine, 4-(phosphonomethyl)-phenylalanine, 3,4,5-trifluoro-D-phenylalanine, 4-benzoyl-DL-phenylalanine, 3,4-difluoro-DL-phenylalanine, cis-4-Fluoro-DL-proline, or (2S,5R)-5-phenyl-pyrrolidine. R6 and R7 may optionally be threo-β-methyl-DL-aspartic acid, DL-2-aminoheptanedioic acid, or alpha-aminosuberic acid.

The synthesis of these and similar analogs of Compound 18 may be conducted analogously to the synthesis of Compound 18, using solid-phase or solution phase peptide synthesis methods known in the art, followed by cyclization.

In addition to variations in one or more side chains, the backbone of Compound 18 can be modified to enhance the stability of the compound. For example, L-Pro-D-Pro can be partially or completely be replaced by dibenzofuran to cyclize the structure. As another option, N-methyl groups can be added to improve molecular stability or to lock the naphthyl group in a particular conformation, or both.

In an alternative embodiment, modifications to the structure of Compound 18 maintain lipophilicity, stability, and ease of synthesis. Compound variations can be synthesized using standard, solid-phase synthesis or other synthetic routes known in the art. In many instances synthesis can be performed on an automatic peptide synthesizer. Analogs of amino acids, beta amino acids, and dibenzofuran group are available from commercial sources.

Figure 1E:
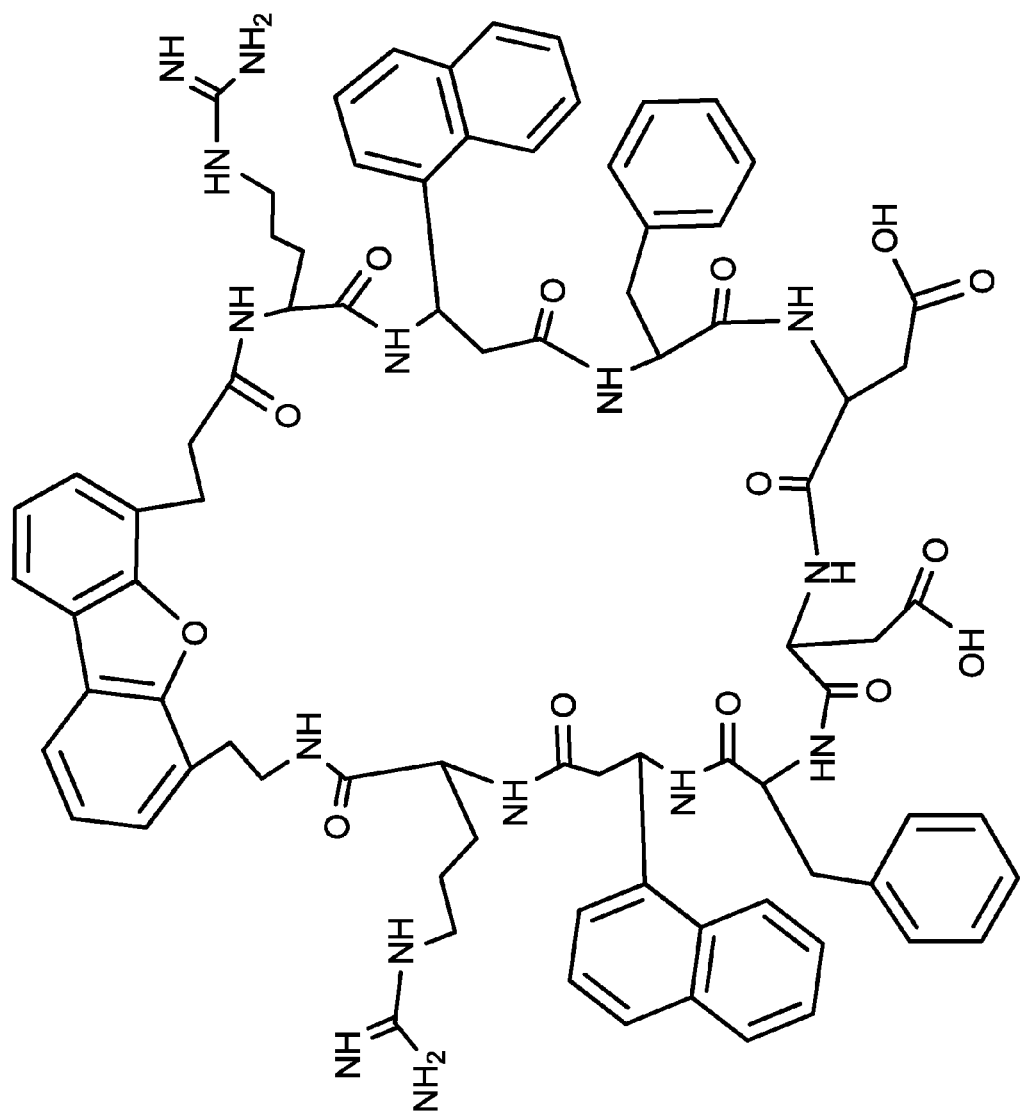
FIGS. 1E and 1F depict modifications of Compound 18 incorporating a dibenzofuran moiety for added stability.
Figure 1F:
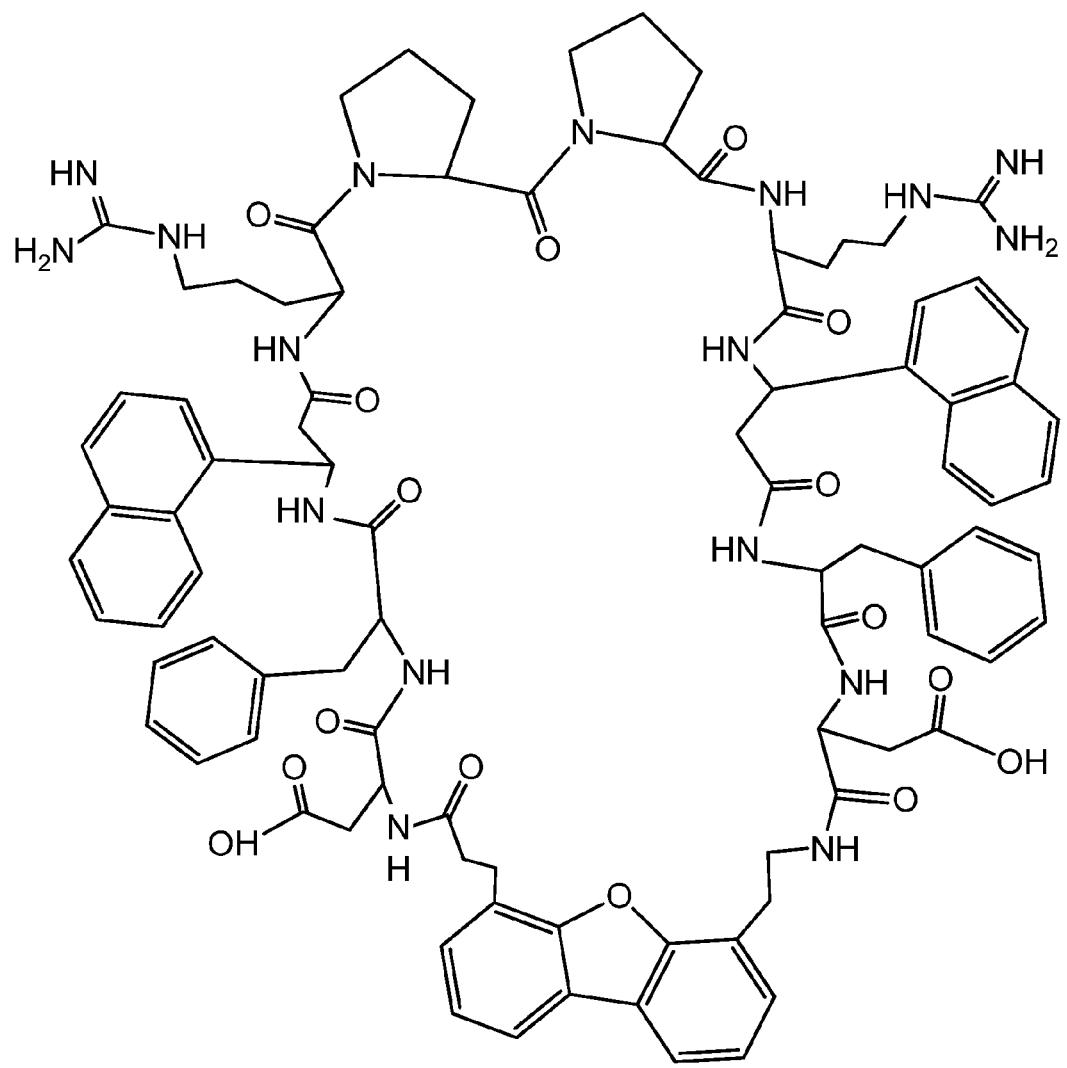
Figure 1G:
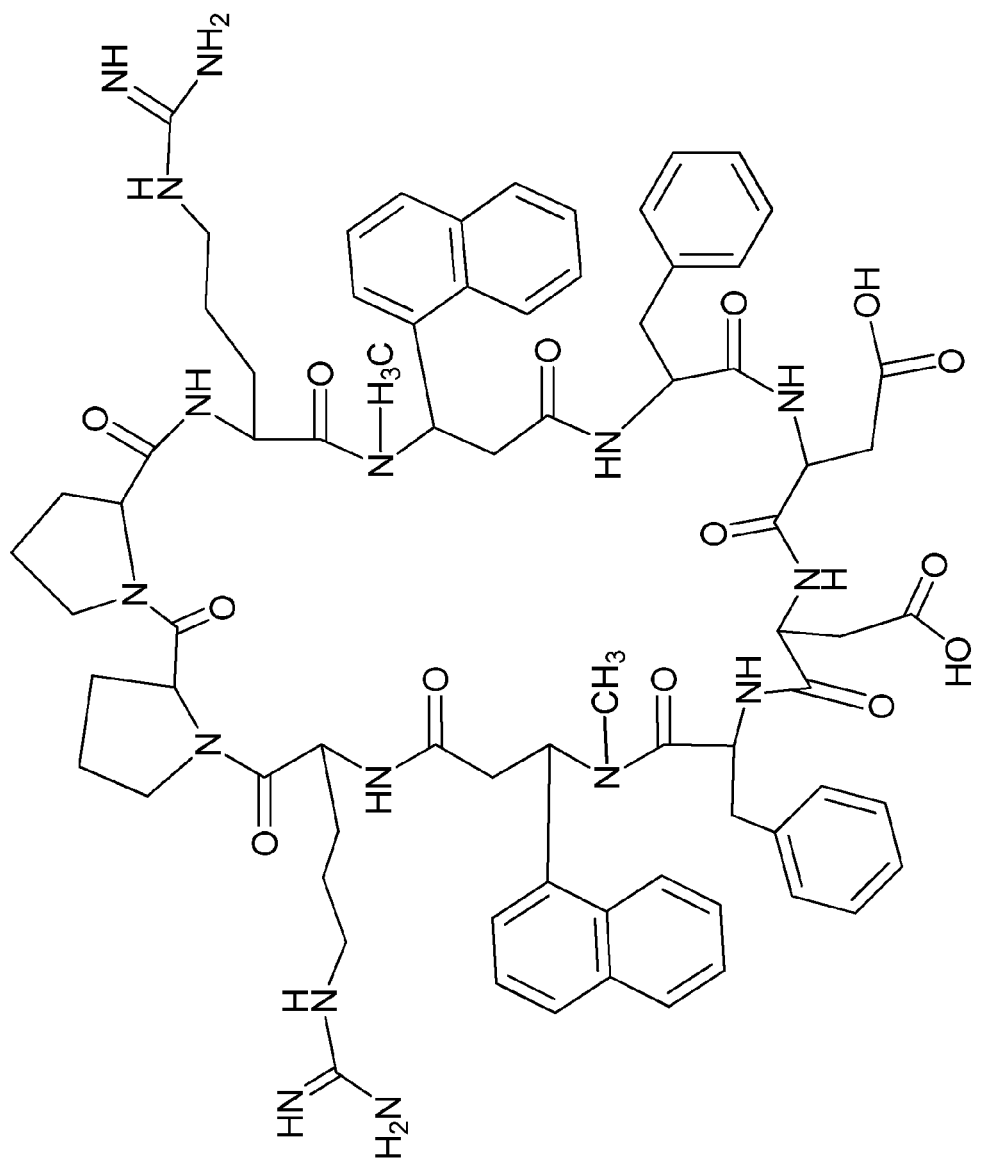
FIG. 1G depicts a modification of Compound 18 with two N-methyl groups for enhanced backbone stability against enzymatic degradation.

FIGS. 1E-1G depict exemplary backbone modifications to Compound 18. FIG. 1E depicts a dibenzofuran moiety incorporated to stabilize the structure. FIG. 1G depicts an N-methyl group incorporated to lock the naphthyl group into a particular orientation and to stabilize the backbone against enzymatic degradation.

Definitions/General Discussion

In discussing the present compounds, compositions, articles, systems, devices, and/or methods, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

While aspects of the present invention may be described or claimed in a particular statutory class, such as the statutory class of compositions of matter, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used in the specification and the claims, the singular forms "a," "an" and "the" include plural referents unless the context clearly dictates otherwise; and vice versa. Thus, for example, reference to "a functional group," "an alkyl," or "a residue" includes mixtures of two or more such functional groups, alkyls, or residues, and the like; and vice versa. Further, a "functional group" or a "group" may consist of just one atom, or it may contain several atoms.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed, and vice versa. It is also understood that each unit between two particular units is also disclosed. For example, if 10 and 15 are disclosed, then 11, 12, 13, and 14 are also disclosed.

References in the specification and claims to parts by weight (or mass) of a particular element or component in a composition denotes the weight (or mass) relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight (or mass) percent (wt. %) of a component, unless specifically stated to the contrary, is based on the total weight (or mass) of the formulation or composition in which the component is included.

As used herein, the terms "optional" or "optionally" means that the subsequently described event or circumstance or component may or may not occur or be included, and that the description includes both instances where said event or circumstance or component occurs or is included and instances where it does not.

As used herein, the term "subject" or "patient" can be a vertebrate, such as a mammal, a fish, a bird, a reptile, or an amphibian. Thus, the subject or patient of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses and embryos, whether male or female, are intended to be covered. In one aspect, the subject is a mammal. A "patient" usually refers to a subject afflicted with a disease or disorder. The term "patient" includes human and veterinary subjects.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removing the cause of the associated disease, pathological condition, or disorder. In addition, this term includes palliative treatment, that is, treatment designed for the relief of symptoms with or without curing the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject who is predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician or veterinarian, and been found to have a condition that can be diagnosed or treated by the compounds, compositions, or methods disclosed herein. As used herein, the phrase "identified to be in need of treatment for a disorder," or the like, refers to selection of a subject based upon need for treatment of the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injections such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "contacting" as used herein refers to bringing a disclosed compound and a cell, target histamine receptor, or other biological entity together in such a manner that the compound can affect the activity of the target (e.g., receptor, cell, etc.), either directly; i.e., by interacting with the target itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause substantial adverse side effects. The specific therapeutically effective dose level for any particular patient will depend upon a variety of factors including the disorder being treated, the severity of the disorder; the specific composition employed; the age, body weight, general health, sex and diet of the patient; the time of administration; the route of administration; the rate of excretion of the specific compound employed; the duration of the treatment; drugs used in combination or coincidentally with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount," that is, an amount effective for prevention of a disease or condition.

As used herein, "$EC_{50}$" is intended to refer to the concentration of a substance (e.g., a compound or a drug) that is required for 50% antagonism of a biological process, or component of a process, including a protein, subunit, organelle, ribonucleoprotein, etc. In one aspect, an $EC_{50}$ can refer to the concentration of a substance that is required for 50% antagonism in vivo. In a further aspect, $EC_{50}$ refers to the concentration of antagonist that provokes a response halfway between the baseline and maximum response.

As used herein, "$IC_{50}$" is intended to refer to the concentration of a substance (e.g., a compound or a drug) that is required for 50% inhibition of a biological process, or component of a process, including a protein, subunit, organelle, ribonucleoprotein, etc. In one aspect, an $IC_{50}$ can refer to the concentration of a substance that is required for 50% inhibition in vivo. In a further aspect, $IC_{50}$ refers to the half maximal (50%) inhibitory concentration (IC) of a substance.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein that, based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

The term "leaving group" refers to an atom (or a group of atoms) with electron withdrawing ability that can be displaced as a stable species, taking with it the bonding electrons. Examples of suitable leaving groups include sulfonate esters, including triflates, mesylates, tosylates, brosylates, and halides.

A residue of a chemical species refers to the moiety that is the product of the chemical species resulting from a particular reaction scheme, or a subsequently formed chemical product, regardless of whether the moiety is actually obtained from the chemical species or from the particular reaction scheme. Thus, an ethylene glycol residue in a polyester refers to one or more —$OCH_2CH_2O$— units in the polyester, regardless of whether ethylene glycol was used to prepare the polyester. Similarly, a sebacic acid residue in a polyester refers to one or more —$CO(CH_2)_8CO$— moieties in the polyester, regardless of whether the residue is obtained by reacting sebacic acid or an ester thereof to obtain the polyester.

As used herein, the term "substituted" is contemplated to include all permissible substitutions in organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more, and they can be the same or different for appropriate organic compounds. Any heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, expressions such as R1, R2, R3, and R4 (and the like) are used as generic symbols to represent various specific substituents. These symbols can refer to any substituent, they are not limited to those disclosed herein, and when they are defined to be certain substituents in one instance, they can, in another instance, be different substituents.

The term "alkyl" refers to a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, optionally substituted alkyl, cycloalkyl, alkoxy, amino, ether, halide, hydroxy, nitro, silyl, sulfo-oxo, or thiol. A "lower alkyl" group is an alkyl group containing from one to six (e.g., from one to four) carbon atoms.

The term "alkyl" is generally used to refer to both unsubstituted alkyl groups and substituted alkyl groups; however, substituted alkyl groups can also be specifically referred to by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups. The term "alkylamino" refers to an alkyl group that is substituted with one or more amino groups. And so forth. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," in which at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, optionally substituted alkyl, cycloalkyl, alkoxy, amino, ether, halide, hydroxy, nitro, silyl, sulfo-oxo, or thiol.

The term "polyalkylene group" is a group having two or more $CH_2$ groups linked to one another. The polyalkylene group can be represented by the formula $-(CH_2)_a-$, where "a" is an integer from 2 to 500.

The terms "alkoxy" and "alkoxyl" to refer to an alkyl or cycloalkyl group bonded through an ether linkage; that is, an "alkoxy" group can be defined as $-OA^1$ where $A^1$ is alkyl or cycloalkyl as defined above. "Alkoxy" also includes polymers of alkoxy groups as just described; that is, an alkoxy can be a polyether such as $-OA^1-OA^2$ or $-OA^1-(OA^2)_a-OA^3$, where "a" is an integer from 1 to 200 and $A^1$, $A^2$, and $A^3$ are alkyl and/or cycloalkyl groups.

The term "alkenyl" is a hydrocarbon group from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol.

The term "cycloalkenyl" is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group, and is included within the meaning of the term "cycloalkenyl," in which at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol.

The term "alkynyl" is a hydrocarbon group of 2 to 24 carbon atoms with a structural formula containing at least one carbon-carbon triple bond. The alkynyl group can be unsubstituted or substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol.

The term "aryl" refers to a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group in which at least one heteroatom is incorporated within the aromatic ring. Examples of heteroatoms include, but are not limited to, nitrogen, oxygen, sulfur, and phosphorus. Likewise, the term "non-heteroaryl," which is also included in the term "aryl," refers to an aromatic group without a heteroatom. The aryl group can be substituted or unsubstituted. The aryl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" refers to a group represented by the formula —C(O)H. "C(O)" is sometimes used as a short hand notation for a carbonyl group, i.e., C=O.

The terms "amine" or "amino" are represented by the formula $-NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group.

The term "alkylamino" is represented by the formula —NH(-alkyl). Representative examples include, but are not limited to, methylamino, ethylamino, propylamino, isopropylamino, butylamino, isobutylamino, (sec-butyl)amino, (tert-butyl)amino, pentylamino, isopentylamino, (tert-pentyl)amino, hexylamino, and the like.

The term "dialkylamino" as used herein is represented by the formula —N(-alkyl)$_2$. Representative examples include, but are not limited to, dimethylamino, diethylamino, dipropylamino, diisopropylamino, dibutylamino, diisobutylamino, di(sec-butyl)amino, di(tert-butyl)amino, dipentylamino, diisopentylamino, di(tert-pentyl)amino, dihexylamino, N-ethyl-N-methylamino, N-methyl-N-propylamino, N-ethyl-N-propylamino, and the like.

The term "carboxylic acid" refers to a compound containing the group —C(O)OH.

The term "ester" refers to a compound containing the group —OC(O)A$^1$ or the group —C(O)OA$^1$, where A$^1$ can be an optionally substituted alkyl, cycloalkyl, alkenyl, cycloalkenyl, alkynyl, cycloalkynyl, aryl, or heteroaryl group.

The term "polyester" refers to a compound having the formula -(A$^1$O(O)C-A$^2$-C(O)O)$_a$— or -(A$^1$O(O)C-A$^2$-OC(O))$_a$—, where A$^1$ and A$^2$ can be, independently, an optionally substituted alkyl, cycloalkyl, alkenyl, cycloalkenyl, alkynyl, cycloalkynyl, aryl, or heteroaryl group, and "a" is an integer from 1 to 500. "Polyester" can be used to describe the polymeric reaction product of a compound having at least two carboxylic acid groups with a compound having at least two hydroxyl groups.

The term "ether" refers to a compound having the formula A$^1$OA$^2$, where A$^1$ and A$^2$ can be, independently, an optionally substituted alkyl, cycloalkyl, alkenyl, cycloalkenyl, alkynyl, cycloalkynyl, aryl, or heteroaryl group.

The term "polyether" refers to a compound having the formula -(A$^1$O-A$^2$O)$_a$—, where A$^1$ and A$^2$ can be, independently, an optionally substituted alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "halide" refers to salts of or other compounds containing one of the halogens: fluorine, chlorine, bromine, and iodine.

The term "heterocycle" refers to single and multi-cyclic aromatic or non-aromatic ring systems in which at least one of the atoms in a ring is an element other than carbon—e.g., N, S, O, P, etc. Heterocycles include for example pyridine, pyrimidine, furan, thiophene, pyrrole, isoxazole, isothiazole, pyrazole, oxazole, thiazole, imidazole, oxazoles, 1,2,3-oxadiazole, 1,2,5-oxadiazole, 1,3,4-oxadiazole, thiadiazoles, 1,2,3-thiadiazole, 1,2,5-thiadiazole, 1,3,4-thiadiazole, triazoles, 1,2,3-triazole, 1,3,4-triazole, tetrazoles, 1,2,3,4-tetrazole and 1,2,4,5-tetrazole, pyridine, pyridazine, pyrimidine, pyrazine, triazines, 1,2,4-triazine and 1,3,5-triazine, tetrazines, 1,2,4,5-tetrazine, pyrrolidine, piperidine, piperazine, morpholine, azetidine, tetrahydropyran, tetrahydrofuran, dioxane, and the like.

The term "hydroxyl" refers to —OH.

The term "ketone" refers to a compound having the formula A$^1$C(O)A$^2$, where A$^1$ and A$^2$ can be, independently, an optionally substituted alkyl, cycloalkyl, alkenyl, cycloalkenyl, alkynyl, cycloalkynyl, aryl, or heteroaryl group.

The term "azide" refers to —N$_3$.

The term "nitro" refers to —NO$_2$.

The term "nitrile" refers to —CN.

The term "silyl" refers to a compound having the formula —SiA$^1$A$^2$A$^3$, where A$^1$, A$^2$, and A$^3$ can be, independently, hydrogen or an optionally substituted alkyl, cycloalkyl, alkoxy, alkenyl, cycloalkenyl, alkynyl, cycloalkynyl, aryl, or heteroaryl group.

The term "sulfo-oxo" refers to the group —S(O)A$^1$, —S(O)$_2$A$^1$, —OS(O)$_2$A$^1$, or —OS(O)$_2$OA$^1$, where A$^1$ can be hydrogen or an optionally substituted alkyl, cycloalkyl, alkenyl, cycloalkenyl, alkynyl, cycloalkynyl, aryl, or heteroaryl group. "S(O)" is sometimes used as a shorthand notation for the group S=O.

The term "sulfonyl" refers to the group —S(O)$_2$A$^1$, where A$^1$ can be hydrogen or an optionally substituted alkyl, cycloalkyl, alkenyl, cycloalkenyl, alkynyl, cycloalkynyl, aryl, or heteroaryl group.

The term "sulfone" refers to a compound having the formula A$^1$S(O)$_2$A$^2$, where A$^1$ and A$^2$ can be, independently, an optionally substituted alkyl, cycloalkyl, alkenyl, cycloalkenyl, alkynyl, cycloalkynyl, aryl, or heteroaryl group.

The term "sulfoxide" refers to a compound having the formula A$^1$S(O)A$^2$, where A$^1$ and A$^2$ can be, independently, an optionally substituted alkyl, cycloalkyl, alkenyl, cycloalkenyl, alkynyl, cycloalkynyl, aryl, or heteroaryl group.

The term "thiol" refers to —SH.

The several R groups depicted in the various Figures can, independently, be chosen to be one or more of the functional groups listed above. As an example, if an R is an amino acid, then one of the hydrogen atoms of the amino acid can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, for "an alkyl group comprising an amino group," the amino group can be incorporated within the backbone of the alkyl group; or alternatively the amino group can be attached to the backbone of the alkyl group.

In general, the compounds of the invention may contain "optionally substituted" moieties. In general, the term "substituted," whether preceded by the term "optionally" or not, means that one or more hydrogens of the designated moiety may be replaced with a suitable substituent. Unless otherwise indicated, an "optionally substituted" group may have a suitable substituent at one, several, or all substitutable positions of the group; and when more than one position is substituted, the substituents may be the same or different at each position. Combinations of substituents are preferably those that result in the formation of stable or chemically feasible compounds. It is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom or heteroatom of an "optionally substituted" group are independently halogen; —(CH$_2$)$_{0-4}$R$^°$; —(CH$_2$)$_{0-4}$OR$^°$; —O(CH$_2$)$_{0-4}$R$^°$, —O—(CH$_2$)$_{0-4}$C(O)OR$^°$; —(CH$_2$)$_{0-4}$CH(OR$^°$)$_2$; —(CH$_2$)$_{0-4}$SR$^°$; —(CH$_2$)$_{0-4}$Ph, which may be substituted with R°; —(CH$_2$)$_{0-4}$O(CH$_2$)$_{0-1}$Ph which may be substituted with R°; —CH=CHPh, which may be substituted with R°; —(CH$_2$)$_{0-4}$O(CH$_2$)$_{0-1}$-pyridyl which may be substituted with R°; —NO$_2$; —CN; —N$_3$; —(CH$_2$)$_{0-4}$ N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$ N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$OC(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$ OC(O)R°; —OC(O)(CH$_2$)$_{0-4}$SR—, SC(S)SR°; —(CH$_2$)$_{0-4}$ SC(O)R°; —(CH$_2$)$_{0-4}$ C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$ OR°; —(CH$_2$)$_{0-4}$OS(O)$_2$R°; —S(O)$_2$NR°$_2$; —(CH$_2$)$_{0-4}$S(O) R°; —N(R°)S(O)$_2$ NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched alkylene)O—N(R°)$_2$; or —(C$_{1-4}$ straight or branched alkylene) C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12- membered saturated, partially unsaturated, or aryl mono- or bicyclic ring having 0-4 heteroatoms independently selected from nitrogen, oxygen, or sulfur, which may optionally be substituted.

Suitable monovalent substituents on R° (or the ring formed by taking two independent occurrences of R° together with their intervening atoms), are independently halogen, —(CH$_2$)$_{0-2}$R$^•$, -(haloR$^•$), —(CH$_2$)$_{0-2}$OH, —(CH$_2$)$_{0-2}$OR$^•$, —(CH$_2$)$_{0-2}$CH(OR$^•$)$_2$; —O(haloR$^•$), —CN, —N$_3$, —(CH$_2$)$_{0-2}$C(O)R$^•$, —(CH$_2$)$_{0-2}$C(O)OH, —(CH$_2$)$_{0-2}$ C(O)OR$^•$, —(CH$_2$)$_{0-2}$SR$^•$, —(CH$_2$)$_{0-2}$SH, —(CH$_2$)$_{0-2}$NH$_2$, —(CH$_2$)$_{0-2}$NHR$^•$, —(CH$_2$)$_{0-2}$NR$^•_2$, —NO$_2$, —SiR$^•_3$, —OSiR$^•_3$, —C(O)SR$^•$, —(C$_{1-4}$ straight or branched alkylene)C(O)OR$^•$, or —SSR$^•$ wherein each R$^•$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6- membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may optionally be substituted, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^•$, -(haloR$^•$), —OH, —OR$^•$, —O(haloR$^•$), —CN, —C(O)OH, —C(O)OR$^•$, —NH$_2$, —NHR$^•$, —NR$^•_2$, or —NO$_2$, wherein each R$^•$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^†$, —NR$^†_2$, —C(O)R$^†$, —C(O)OR$^†$, —C(O)C(O)R$^†$, —C(O)CH$_2$C(O) R$^†$, —S(O)$_2$R$^†$, —S(O)$_2$NR$^†_2$, —C(S)NR$^†_2$, —C(NH)NR$^†_2$, or —N(R$^†$)S(O)$_2$R$^†$; wherein each R$^†$ is independently hydrogen, C$_{1-6}$ aliphatic which may optionally be substituted, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^†$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^†$ are independently halogen, —R$^•$, -(haloR$^•$), —OH, —OR$^•$, —O(haloR$^•$), —CN, —C(O)OH, —C(O)OR$^•$, —NH$_2$, —NHR$^•$, —NR$^•_2$, or —NO$_2$, wherein each R$^•$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

The term "organic residue" defines a carbon-containing residue, i.e., a residue comprising at least one carbon atom, and includes but is not limited to the carbon-containing groups, residues, or radicals. Organic residues can contain various heteroatoms, or be bonded to another molecule through a heteroatom, including oxygen, nitrogen, sulfur, phosphorus, or the like. Examples of organic residues include but are not limited to alkyl or substituted alkyl, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A term closely related to "residue" is "radical," which refers to a fragment, group, or substructure of a molecule described herein, regardless of how the molecule is prepared. For example, a 2,4-thiazolidinedione radical in a particular compound has the structure:

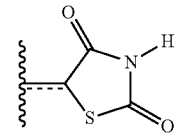

regardless of whether thiazolidinedione is used to prepare the compound. In some embodiments the radical (for example an alkyl radical) can be further modified (i.e., into a substituted alkyl radical) by bonded to it one or more "substituent radicals." The number of atoms in a given radical is not critical to the present invention unless indicated otherwise.

"Organic radicals" are those containing one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen atoms bound to some or all of the carbon atoms. An example of an organic radical that contains no heteroatoms is a 5,6,7,8-tetrahydro-2-naphthyl radical. In some embodiments, an organic radical can contain 1-10 heteroatoms bound thereto or therein, heteroatoms including halogens, oxygen, sulfur, nitrogen, phosphorus, and the like. Examples of organic radicals include but are not limited to alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, and substituted heterocyclic radicals. A few non-limiting examples of organic radicals that include heteroatoms include alkoxy radicals, trifluoromethoxy radicals, acetoxy radicals, dimethylamino radicals, and the like.

"Inorganic radicals" are those containing no carbon atoms. Inorganic radicals comprise bonded combinations of atoms selected from, for example, hydrogen, nitrogen, oxygen, silicon, phosphorus, sulfur, selenium, and halogens such as fluorine, chlorine, bromine, and iodine, which can be present individually or bonded together in chemically stable combinations. Inorganic radicals have 10 or fewer, or preferably one to six or one to four non-carbon atoms. Examples of inorganic radicals include, but are not limited to, amino, hydroxy, halogens, nitro, thiol, sulfate, phosphate, and the like. Unless otherwise specifically indicated, inorganic radicals generally do not have covalently bonded therein any metallic atoms (such as the alkali metals, alkaline earth metals, transition metals, lanthanide metals, or actinide metals), although such metal ions can nevertheless sometimes serve as a pharmaceutically acceptable cation for anionic inorganic radicals such as a sulfate, phosphate, or other anionic inorganic radical. Inorganic radicals generally do not include metal or metalloid atoms such as boron, aluminum, gallium, germanium, arsenic, tin, lead, or tellurium, unless otherwise specifically indicated.

Compounds described herein can contain one or more double bonds and, thus, potentially give rise to cis/trans (E/Z) isomers, as well as other conformational isomers. Unless stated to the contrary, the invention includes each such possible isomer, as well as mixtures of such isomers.

Unless stated to the contrary, a formula with chemical bonds shown only as solid lines and not as wedges or dashed lines contemplates each possible isomer, e.g., each enantiomer and diastereomer, and each mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these compounds, called stereoisomers, are identical except that (at each chiral center) they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. A chiral carbon atom is sometimes designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. In accordance with usage in the art, when it is desired to specify the absolute configuration about a chiral carbon, one of the bonds to the chiral carbon can be depicted as a wedge (bonds to atoms above the plane) and the other can be depicted as a series or wedge of short parallel lines (bonds to atoms below the plane). The standard Cahn-Ingold-Prelog system can be used to assign the (R) or (S) configuration to a chiral carbon.

When the disclosed compounds contain one chiral center, the compounds exist in two enantiomeric forms. Unless specifically stated to the contrary, a disclosed compound includes both enantiomers and mixtures of enantiomers, such as the specific 50:50 mixture commonly referred to as a racemic mixture. The enantiomers can be resolved by methods known to those skilled in the art, such as formation of diastereomeric salts which may be separated, for example, by crystallization (see, CRC Handbook of Optical Resolutions via Diastereomeric Salt Formation by David Kozma (CRC Press, 2001)); formation of diastereomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step can liberate the desired enantiomeric form. Alternatively, specific enantiomers can be synthesized by asymmetric synthesis using optically active reagents, substrates, catalysts or solvents, or by converting one enantiomer into the other by asymmetric transformation.

Designation of a specific absolute configuration at a chiral carbon in a disclosed compound is understood to mean that the designated enantiomeric form of the compounds is present in enantiomeric excess. Enantiomeric excess, as used herein, is the presence of a particular enantiomer at a ratio greater than 50%, for example, greater than 60%, greater than 70%, greater than 75%, greater than 80%, greater than 85%, greater than 90%, greater than 95%, greater than 98%, or greater than 99%. In one aspect, the designated enantiomer is substantially free from the other enantiomer. For example, the "R" forms of the compounds can be substantially free from the "S" forms of the compounds and are, thus, in enantiomeric excess of the "S" forms. Conversely, "S" forms of the compounds can be substantially free of "R" forms of the compounds and are, thus, in enantiomeric excess of the "R" forms.

When a disclosed compound has two or more chiral carbons, it can have more than two optical isomers and can generally exist in so-called diastereomeric forms. For example, when there are two chiral carbons, the compound can have up to four optical isomers and two pairs of enantiomers ((S,S)/(R,R) and (R,S)/(S,R)). The pairs of enantiomers (e.g., (S,S)/(R,R)) are mirror image stereoisomers of one another. The stereoisomers that are not mirror-images (e.g., (S,S) and (R,S)) are diastereomers. The diastereoisomeric pairs can be separated from one another by standard (non-stereoselective) methods known to those skilled in the art, for example by chromatography or crystallization; and if desired the individual enantiomers within a pair may be separated as described above. Unless otherwise specifically excluded, a disclosed compound includes each diastereoisomer of such compounds and mixtures thereof.

Compounds described herein comprise atoms in both their natural isotopic abundance and in non-natural isotopic abundance. The disclosed compounds can be isotopically-labeled or isotopically-substituted compounds identical to those described, but for the fact that one or more atoms are replaced by an atom having an atomic mass or mass number different from the atomic mass or mass number typically found in nature on the Earth. Examples of isotopes that can be incorporated into compounds of the invention include isotopes of hydrogen, carbon, nitrogen, oxygen, phosphorous, fluorine and chlorine, such as $^2$H or $^3$H, $^{13}$C or $^{14}$C, $^{15}$N, $^{18}$O or $^{17}$O, $^{35}$S, $^{18}$F, and $^{36}$Cl, respectively. Compounds that comprise prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^3$H and $^{14}$C are incorporated, which are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, $^2$H, can afford certain therapeutic advantages resulting from greater metabolic stability, for example increased in vivo half-life or reduced dosage requirements and, hence may be preferred in some circumstances. Isotopically-labeled compounds of the present invention and prodrugs thereof can generally be prepared by carrying out the procedures below, by substituting a readily available isotopically labeled reagent for a non-isotopically labeled reagent.

The compounds of the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvate or water molecules can coordinate with the compounds of the invention to form hydrates or other solvates. Unless stated to the contrary, the invention includes all such possible hydrates and solvates.

The term "co-crystal" means a physical association of two or more compounds in a definite stoichiometric ratio in a single crystalline structure. See e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. An example of a co-crystal is that formed from p-toluenesulfonic acid and benzenesulfonic acid.

Some compounds have multiple solid phases of matter, sometimes termed polymorphic forms or modifications. The different modifications of a polymorphic substance can differ, sometimes greatly, in their physical properties. The compounds according to the invention can be present in different polymorphic forms, with it being possible for particular modifications to be metastable. Unless stated to the contrary, the invention includes all such possible polymorphic forms.

Certain materials, compounds, compositions, and components disclosed herein can be obtained commercially or can be readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated or clearly implied by context, it is not intended that any method set forth herein should be construed as requiring that its steps be performed in a specific order. Accordingly, where a method claim does not actually recite an order to be followed by its steps or it is not otherwise specifically stated in the claims or descriptions that the steps are to be limited to a specific order, it is not intended that an order be inferred, unless clearly required by context. This principle also holds for any possible non-express basis for interpretation, including: matters of logic with respect to arrangement of steps or operational flow; plain meaning derived from grammatical organization or punctuation; and the number or type of embodiments described in the specification. Those of skill in the art will recognize that, in some instances, it is implicit that at least some of the steps of an organic synthesis or of a separation should be carried out in a particular order to produce the desired result.

Disclosed are the components used to prepare the compositions of the invention as well as the compositions themselves to be used within the methods disclosed herein. These and other materials are disclosed herein, and it is understood that when combinations, subsets, interactions, groups, etc. of these materials are disclosed that, while specific reference of each of the various individual and collective combinations and permutations of these compounds cannot be explicitly disclosed, each is specifically contemplated and described herein. For example, if a particular compound is disclosed and discussed and a number of modifications that can be made to a number of molecules including those compounds are discussed, specifically contemplated is each and every combination and permutation of the compound and the modifications that are possible unless specifically indicated to the contrary. Thus, if a class of molecules A, B, and C is disclosed, as well as a class of molecules D, E, and F; and an example of a combination molecule, A-D is disclosed, then even if each is not individually recited each is individually and collectively contemplated, meaning combinations such as A-E, A-F, B-D, B-E, B-F, C-D, C-E, and C-F, etc. Likewise, any subset or combination of such combinations is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural features for performing the disclosed functions, and it is understood that there are a variety of structures that can perform the same function that are related to the disclosed structures, provided these structures will achieve the same or a similar result.

In one aspect, the invention relates to compounds useful for inhibiting cancers, particularly cancers that overexpress HER2. The compound may be supplied in solid form, or dissolved in water or alcohol (preferably ethanol).

It is contemplated that each disclosed derivative can be optionally further substituted. It is also contemplated that any one or more derivatives can be optionally omitted from the invention. It is understood that a disclosed compound can be provided by the disclosed methods. It is also understood that the disclosed compounds can be employed in the disclosed methods of use.

The structure of the disclosed compounds may be modified to maintain or enhance activity against tumors, or to maintain or enhance desirable physical properties such as heat stability, stability at different pH, and the like. Each chiral center, when present, is independently selected from the R- and S-stereoisomer, or a racemic mixture thereof.

The compound may be isolated or prepared in substantially pure form; where, for this purpose, "substantially pure" means that the compound is present in a composition in a concentration (by mass) greater than or equal to: 50%, 55%, 60%, 65%, 70%, 75%, 80%, 85%, 90%, 95%, 96%, 97%, 98%, 99%, 99.5%, 99.7%, or 99.9%.

A "substantially pure" mixture of two or more stereoisomers refers to a composition in which the stereoisomers are present in any proportion(s) relative to one another, and in which the combined total amount of all stereoisomers (by mass) in the composition is greater than or equal to: 50%, 55%, 60%, 65%, 70%, 75%, 80%, 85%, 90%, 95%, 96%, 97%, 98%, 99%, 99.5%, 99.7%, or 99.9%.

In one aspect, the disclosed compounds comprise the products of the synthetic methods described herein. In a further aspect, the disclosed compounds comprise a compound produced by a synthetic method described herein. In a still further aspect, the invention comprises a pharmaceutical composition comprising a therapeutically effective amount of the product of the disclosed methods and a pharmaceutically acceptable carrier. In a still further aspect, the invention comprises a method for manufacturing a medicament comprising combining at least one compound of any of disclosed compounds or at least one product of the disclosed methods with a pharmaceutically acceptable carrier or diluent.

Compounds of the present invention may be administered in pharmaceutical compositions to treat patients (humans and other mammals) with cancer. Thus, the invention includes pharmaceutical compositions containing at least one compound from the present invention and a pharmaceutically acceptable carrier. A composition of the invention may further include at least one other therapeutic agent, for example, a combination formulation or combination of differently formulated active agents for use in a combination therapy method.

The present invention also features methods of using or preparing or formulating such pharmaceutical compositions. The pharmaceutical compositions can be prepared using conventional pharmaceutical excipients and compounding techniques known to those skilled in the art of preparing dosage forms. It is anticipated that the compounds of the invention can be administered by oral, parenteral, rectal, topical, or ocular routes, or by inhalation. Preparations may also be designed to provide slow release of the active ingredient. The preparation may be in the form of tablets, capsules, sachets, vials, powders, granules, lozenges, powders for reconstitution, liquid preparations, or suppositories. Preferably, compounds may be administered by intravenous infusion or topical administration, but more preferably by oral administration.

For oral administration, the compounds of the invention can be provided in the form of tablets or capsules, or as a solution, emulsion, or suspension. Tablets for oral use may include the active ingredient mixed with pharmaceutically acceptable excipients such as inert diluents, disintegrating agents, binding agents, lubricating agents, sweetening agents, flavoring agents, coloring agents and preservatives. Suitable inert fillers include sodium and calcium carbonate, sodium and calcium phosphate, lactose, starch, sugar, glucose, methyl cellulose, magnesium stearate, mannitol, sorbitol, and the like; typical liquid oral excipients include ethanol, glycerol, water and the like. Starch, polyvinylpyrrolidone, sodium starch glycolate, microcrystalline cellulose, and alginic acid are suitable disintegrating agents. Binding agents may include starch and gelatin. The lubricating agent, if present, will generally be magnesium stearate, stearic acid or talc. If desired, the tablets may be coated with a material such as glyceryl monostearate or glyceryl distearate to delay absorption in the gastrointestinal tract, or may be coated with an enteric coating. Capsules for oral use include hard gelatin capsules in which the active ingredient is mixed with a solid, semi-solid, or liquid diluent, and soft gelatin capsules wherein the active ingredient is mixed with water, an oil such as peanut oil or olive oil, liquid paraffin, a mixture of mono and di-glycerides of short chain fatty acids, polyethylene glycol 400, or propylene glycol.

Liquids for oral administration may be suspensions, solutions, emulsions or syrups or the compound may be provided as a dry product for reconstitution with water or other suitable vehicles before use. Liquid compositions for oral administration may contain pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, which include oils (for example, almond oil or fractionated coconut oil), propylene glycol, ethyl alcohol or water; preservatives (for example, methyl or propyl p-hydroxybenzoate or sorbic acid); wetting agents or emulsifiers such as lecithin; and, if needed, flavoring or coloring agents.

The compounds of this invention may also be administered by non-oral routes. The compositions may be formulated for rectal administration as a suppository. For parenteral use, including intravenous, intramuscular, intraperitoneal, or subcutaneous routes, the compounds of the invention will generally be provided in sterile aqueous solutions or suspensions, buffered to an appropriate pH and isotonicity or in parenterally acceptable oil. Suitable aqueous vehicles include Ringer's solution and isotonic sodium chloride. Such forms will be presented in unit dose form such as ampoules or disposable injection devices, in multi-dose forms such as vials from which the appropriate dose may be withdrawn, or in a solid form or pre-concentrate that can be used to prepare an injectable formulation. Another mode of administration of the compounds of the invention may utilize a patch formulation to affect transdermal delivery. The compounds of this invention may also be administered by inhalation, via the nasal or oral routes using a spray formulation containing the compound of the invention and a suitable carrier.

Methods are known in the art for determining effective doses for therapeutic (treatment) and prophylactic (preventative) purposes for the pharmaceutical compositions or the drug combinations of the present invention, whether or not formulated in the same composition. The specific dosage level required for any particular patient will depend on a number of factors, including severity of the condition being treated, the route of administration, and the weight of the patient. For therapeutic purposes, "effective dose" or "effective amount" refers to that amount of each active compound or pharmaceutical agent, alone or in combination, that elicits the biological or medicinal response in a tissue, system, animal, or human that is being sought by a researcher, veterinarian, medical doctor, or other clinician, which includes alleviation of the symptoms of the disease or disorder being treated. For prophylactic purposes (i.e., preventing or inhibiting the onset or progression of a disorder), the term "effective dose" or "effective amount" or "therapeutically effective dose" or "therapeutically effective amount" refers to that amount of each active compound or pharmaceutical agent, alone or in combination, that inhibits in a subject the onset or progression of a cancer as being sought by a researcher, veterinarian, medical doctor, or other clinician, in which the cancer overexpresses HER2. Methods of combination therapy include co-administration of a single formulation containing all active agents; essentially contemporaneous administration of more than one formulation; and administration of two or more active agents separately formulated.

It is expected that a dose of about 15 mg to about 55 mg intravenously three times per week, or about 45 mg to about 150 mg oral three times a week will be effective for treatment. Expressed as dosage per unit body weight, a typical dose is expected to be between about 0.2 mg/kg and about 0.75 mg/kg (IV), or about 0.6 to about 2 mg/kg (oral), three times per week in either case. Actual dosages may, of course, be adjusted higher or lower depending on clinical observations and outcomes. Alternatively, the doses can be administered at higher frequency earlier in the treatment course, and then adjusted later to a lower frequency—e.g., daily for the first three weeks, and thereafter three times per week.

Some compounds of the invention may be orally dosed in the range of about 0.05 to about 50 mg/kg daily, others may be dosed at about 0.05 to about 20 mg/kg daily, while still others may be dosed at 0.1 to about 10 mg/kg daily. Infusion doses can be administered from about 1 to about 1000 µg/kg/min, admixed with a pharmaceutically-acceptable carrier, over a period ranging from several minutes to several days. For topical administration compounds of the present invention may be mixed with a pharmaceutically-acceptable carrier at a concentration of about 0.1% to about 10% of drug to vehicle.

It will be appreciated that, although specific embodiments of this invention have been described herein for purpose of illustration, various modification may be made without departing from the spirit and scope of the invention.

The following examples are put forth to provide those of ordinary skill in the art with a complete disclosure and description of how the compounds, compositions, articles, devices and/or methods claimed herein are made and evaluated. The examples are intended to be exemplary, but not to limit the scope of the invention. Efforts have been made to ensure accuracy with respect to numbers (e.g., amounts, temperature, etc.), but some errors and deviations should be accounted for. Unless indicated otherwise, parts are parts by weight (mass), temperature is measured in the Celsius scale (° C.) or the temperature is ambient temperature, and pressure is at or near one atmosphere.

Methods and Results

TABLE 1

Abbreviations

| | |
|---|---|
| EGFR | Epidermal growth factor receptors |
| HER | Human epidermal growth factor receptors |
| PPI | Protein-protein interactions |
| Anapa | 3-amino-3-(1-napthyl propionic acid) |
| PLA | Proximity ligation assay |

TABLE 2

Materials

| | |
|---|---|
| Compound 18 | An embodiment of the present invention |
| Compounds 5 and 9 | Previously studied compounds |
| Compound 21 | Previously studied compound |
| CP | A control peptidomimetic |
| Lapatinib | A drug compound in clinical use for breast cancer therapy; a HER2 and EGFR kinase inhibitor |
| BT-474 and SKBR-3 | Breast cancer cell lines |
| SKOV-3 | Ovarian cancer cell line |
| Calu-3 | Lung cancer cell line |
| MCF-7 | Breast cancer cell line that does not overexpress HER2 |
| MCF-10A | Normal breast epithelial cell line |
| U2OS | Bone osteosarcoma cell line |

Example 1. Compound 18: Synthesis and Characterization

Compound 18 was synthesized using standard solid phase Fmoc chemistry. 2-Chlorotrityl chloride resin (3 g, 0.89 mmol/g) was swollen in 30 mL of dichloromethane for 30 minutes. The resin was then loaded with a solution of Fmoc-Pro-OH (900 mg, 2.67 mmol) and DIEA (2.325 mL, 13.35 mmol) in 30 mL of dichloromethane. The resin mixture was agitated for 2 hours and then filtered and washed with NMP (30 mL, 6×30 sec), DCM/MeOH/DIEA (80:15:5, 2×15 min), NMP (5×30 sec), and dichloromethane (5×30 sec). The resin was dried under vacuum overnight, after which the substitution level was checked by UV absorption of the Fmoc-piperdine adduct. After the substitution level had been determined, the resin was swollen with DMF (2×10 min) and then deprotected with 30 mL of 20% piperidine/NMP (2×5 min). The resin was then washed with DMF (5×30 sec) and dichloromethane (5×30 sec) and dried under vacuum overnight. The deprotected resin was stored under an inert atmosphere at −20° C. Using an automatic peptide synthesizer the remaining portion of Compound 18 was synthesized. H-Pro-CTC resin (91 mg, 0.55 mmol/g, 50 μmol) was place in a 10 mL reaction vessel which was placed on the synthesizer. The resin was swollen on the synthesizer in DMF (1×30 min) as part of the first coupling cycle. All amino acids were coupled using 5 equivalents of Fmoc-protected amino acid, and 5 equivalents of HCTU dissolved in 2 mL of a 0.4M solution of 4-methylmorpholine in NMP. The amino acid solution was bubbled on the instrument for 2 minutes before it was added to the resin, after which the resin was shaken for 30 minutes. The resin was then washed with DMF (5×30 sec), then deprotected with 20% piperidine/NMP (2×5 min), and then washed again with DMF (5×30 sec). This sequence was repeated for each of the remaining amino acids in the sequence. After the last amino acid had been added to the peptide, the final Fmoc protecting group was removed as before, followed by washing. The peptide was cleaved from the resin by adding 2,2,2-trifluoroethanol:dichloromethane (2 mL, 1:1) to the resin and agitating for 3 hours. The cleavage step was repeated 3 times. The three cleavage solutions were then combined, and the solvent was evaporated at room temperature under a gentle stream of nitrogen. The remaining solid was dissolved in 100 mL of THF/DMF (4:1) to which was added PyAOP (4 eq., 104 mg) and DIEA (7 eq, 70 μL). The solution was agitated for 2 hours, after which the solvent was evaporated under vacuum to yield a solid. The crude peptide was then treated with a deprotection cocktail (4 mL of TFA:water:TIPS, 95:2.5:2.5) for 3 hours. The peptide solution was poured into a 50 mL centrifuge tube, and the peptide precipitated with 30 mL of cold diethyl ether. The tube containing the peptide was centrifuged for 10 minutes, and the supernatant was removed. The peptide pellet was broken up in 30 mL of cold diethyl ether and again centrifuged as before. This process was repeated 4 times. The solid was dissolved in 4 L of 0.1% TFA/water, frozen, and lyophilized to yield a white powder as the crude peptide.

Figure 2:
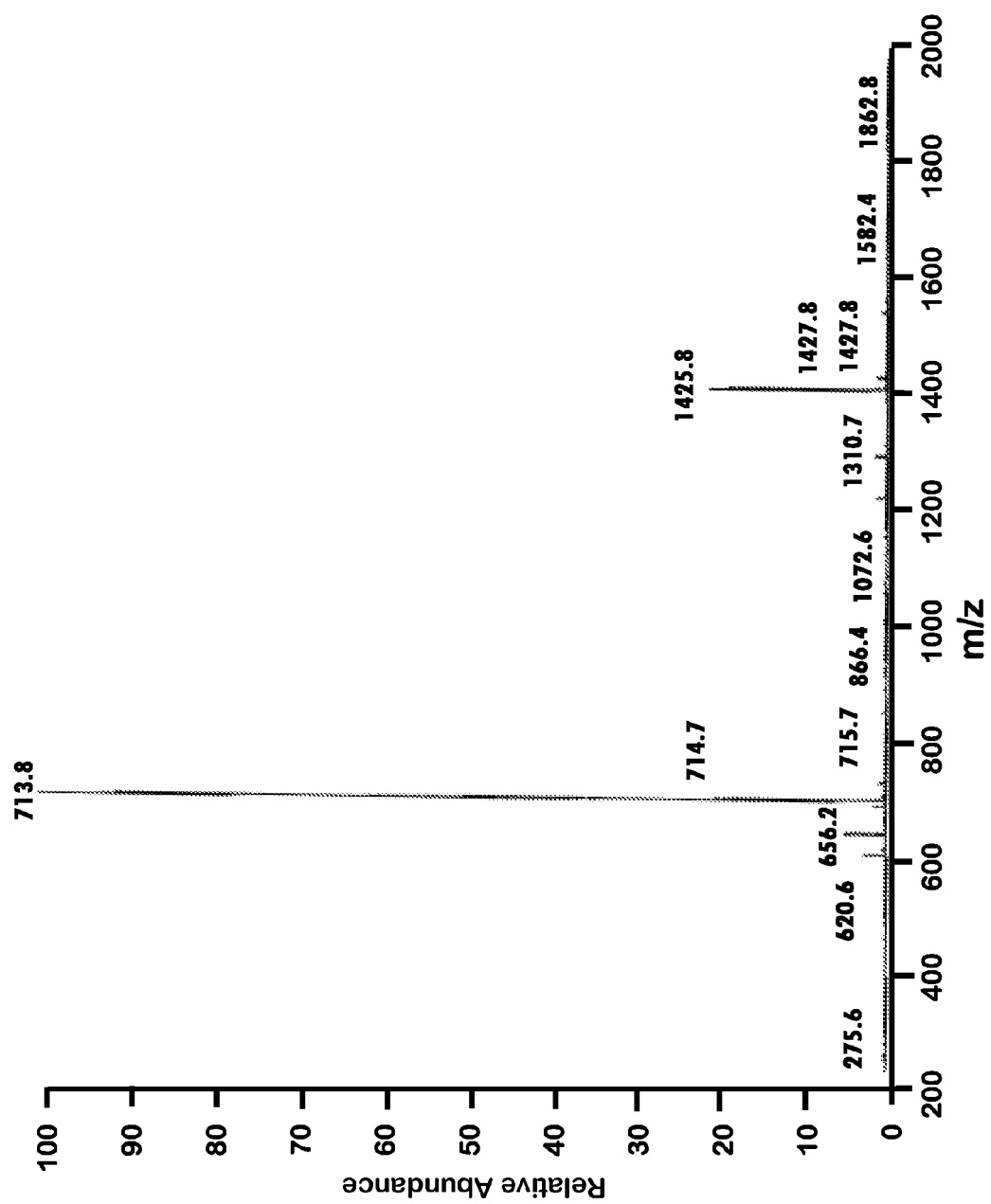
FIG. 2 depicts an LC-MS analysis of Compound 18.

The resulting Compound 18 was characterized by LC-MS and $^1$H 2D-NMR. FIG. 2 depicts a typical LC-MS mass spectrum, showing singly (1425.8) and doubly charged (713.8) ions, corresponding to the calculated molecular weight for Compound 18. An $^1$H 2D-TOCSY NMR spectrum confirmed the amino acids and Anapa present in the compound (data not shown).

Compound 18 contained the L-amino acids Arg, Phe, and Asp. The β-naphthyl moiety was itself a racemic mixture in the initial embodiment. Hence, Compound 18 as originally prepared was thus a mixture of four stereoisomers for the β-naphthyl moieties: (R, S), (S, R), (S, S), and (R, R).

Example 2. Inhibition Testing

Compound 18 was evaluated for its ability to inhibit the growth of cells in various cancer cell lines using the CellTiterGlo™ assay. Antiproliferative activity was determined from a dose-response curve as the $IC_{50}$ value, shown in Table 3. Compound 18 exhibited antiproliferative activity against different types of cancer cells, particularly HER2-positive cancer cells such as breast cancer cell lines BT-474 and SKBR-3, ovarian cancer cell line SKOV-3, and lung cancer cell line Calu-3, for each of which the $IC_{50}$ values were in the sub-micromolar range. In breast cancer cell line MCF-7, which does not overexpress HER2, the $IC_{50}$ value for Compound 18 was greater than 50 μM. For the control, normal breast epithelial cell line MCF-10A, Compound 18 exhibited antiproliferative activity with an $IC_{50}$ value of 40 μM (data for MCF-10A not included in Table 3).

Compound 18 was not toxic to normal cells at doses that were toxic to cancer cells. The antiproliferative activity of Compound 18 against the normal MCF-10A cell line was nearly 200 times less than its activity against the SKBR-3 cancer cell line. Compared to lung cancer cell line (Calu-3), Compound 18 was nearly 2000 times less active against the normal MCF-10A cell line.

TABLE 3

| Compound | Structure | Mol. Wt. | $IC_{50}$ (μM) | | | | |
|---|---|---|---|---|---|---|---|
| | | | BT-474 (+) | SKBR-3 (+) | MCF-7 (−) | SKOV-3 (+) | Calu-3 (+) |
| 5 | H₂N-R(Anapa)F-OH | 519 | 0.895 ± 0.029 | 0.396 ± 0.022 | 16.9 ± 1.0 | 0.658 ± 0.04 | 0.601 ± 0.02 |
| 9 | H₂N-R(Anapa)FD-OH | 636 | 0.785 ± 0.011 | 0.445 ± 0.032 | 45 | 0.417 ± 0.055 | 0.847 ± 0.071 |
| 18 | Cyclo(1,10)PpR(Anapa)FDDF(Anapa)R | 1425 | 0.197 ± 0.055 | 0.194 ± 0.046 | >50 | 0.853 ± 0.102 | 0.018 ± 0.013 |
| 21 | Ac-f(Anapa)r-NH₂ | 559 | 0.595 ± 0.27 | 0.373 ± 0.150 | >50 | 0.373 ± 0.15 | 1.09 ± 0.31 |
| CP | H₂N-K(3-aminobiphenyl propionic acid)F-OH | 516.3 | >100 | >100 | >100 | >100 | >100 |
| | Lapatinib | | | 0.025 ± 0.004 | | | |

Table 3 Notes:
Compounds were tested for antiproliferative activity against several cancer cell lines and a control cell line. All compounds had purity >90% by HPLC analysis. CP was the control peptidomimetic. Small letters in a sequence refer to D-amino acids, and capital letters refer to L-amino acids. Anapa is 3-amino-3-(1-napthyl propionic acid). BT-474 and SKBR-3 are HER2-overexpressing breast cancer cells. MCF-7 are normal breast cancer cells that do not overexpress HER2. SKOV-3 and Calu-3 are HER2-overexpressing ovarian and lung cancer cells, respectively. (+) and (−) indicate HER2-positive and HER2-negative, respectively.

Example 3. Competitive Binding Assays

Figure 3:
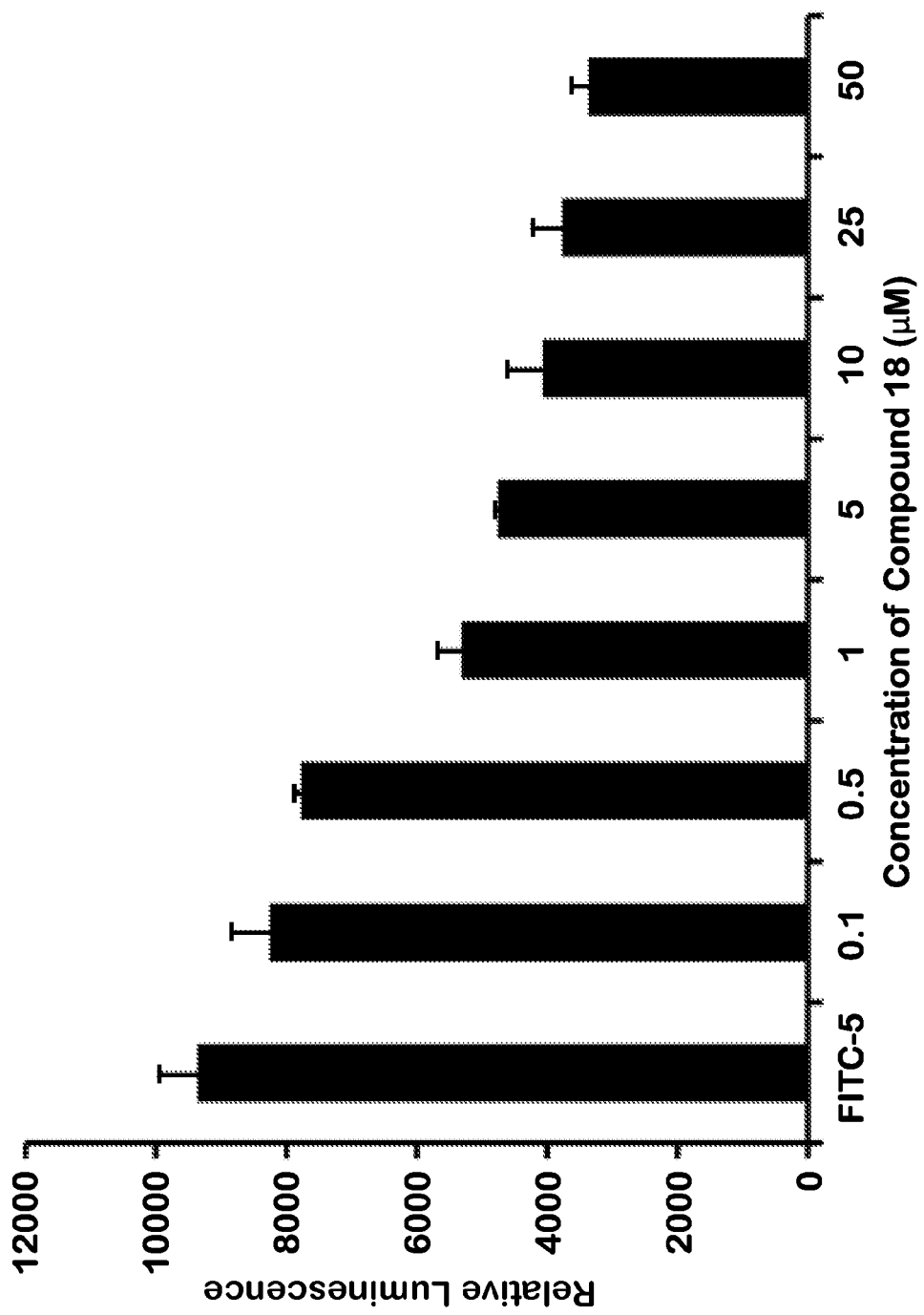
FIG. 3 depicts results for a competitive binding assay for Compound 18 competing with Compound 5.

Compound 18 is highly specific for HER2-positive cancers. Compound 18 targets the PPI of EGFR extracellular domain IV. To confirm that Compound 18 binds this target protein, a competitive binding assay was conducted with another compound known to bind to HER2 domain IV. FITC-labeled Compound 5 and various concentrations of Compound 18 were incubated with BT-474 cells. A decrease in fluorescence indicated that Compound 18 had bound to BT-474 cells expressing HER2 protein. As shown in FIG. 3, Compound 18 bound to HER2 and competitively inhibited fluorescently-labeled Compound 5.

Example 4. Testing Compound 18 Analogs for PPI Inhibition

Analogs of Compound 18 were tested for PPI inhibition of EGFR and antiproliferative activity against the different cancer cell lines described above. All compounds had >90% purity by HPLC analysis. The structures of these compounds are shown in FIGS. 1E and 1F. Observed antiproliferative activity is summarized in Table 4 and Table 5.

TABLE 4

| Com- | Antiproliferative activity $IC_{50}$ (µM) | | | |
|---|---|---|---|---|
| pound | SKBR-3 | BT-474 | Calu-3 | MCF-7 |
| 18D | 0.241 ± 0.098 | 0.327 ± 0.109 | 0.488 ± 0.126 | 35.6 ± 4.6 |
| 18E | 0.216 ± 0.015 | 0.811 ± 0.085 | 0.779 ± 0.191 | 53.9 ± 3.1 |

TABLE 5

| | | Antiproliferative activity $IC_{50}$ (µM) | | | |
|---|---|---|---|---|---|
| Compound | Structure | BT-474 | MCF-7 | SKBR-3 | Calu-3 |
| 33 | Cyclo(PpR-(R)Anapa-FDDF-(R)Anapa-K | 0.4 ± 0.14 | >100 | 0.5 ± 0.28 | 0.9 ± 0.2 |
| 38 | Cyclo(Ppr-(R)Anapa-fddf-(R)Anapa-r | 0.86 ± 0.05 | 13.5 ± 0.7 | 0.8 ± 0.07 | 0.55 ± 0.2 |
| 40 | Cyclo(Ppdf-(R)Anapa-rdf-(R)Anapa-r | 0.29 ± 0.16 | N.D | N.D | N.D |
| 41 | Cyclo(Ppr-(R)Anapa-fdr-(R)Anapa-fd | 0.85 ± 0.07 | N.D | N.D | N.D |

Notes to Tables 4 and 5:

Several analogs of Compound 18 were designed with D-amino acids or chain reversal. Antiproliferative activity was measured against different cancer cell lines. All compounds had purity >90% by HPLC analysis. N.D="Not Determined." Capital letters refer to L-amino acids, and small letters refer to D-amino acids. The D-amino acid substituted compounds showed stability against enzymes in serum.

Example 5. Dose-Response Curves for Heterodimerization

Figure 4A:
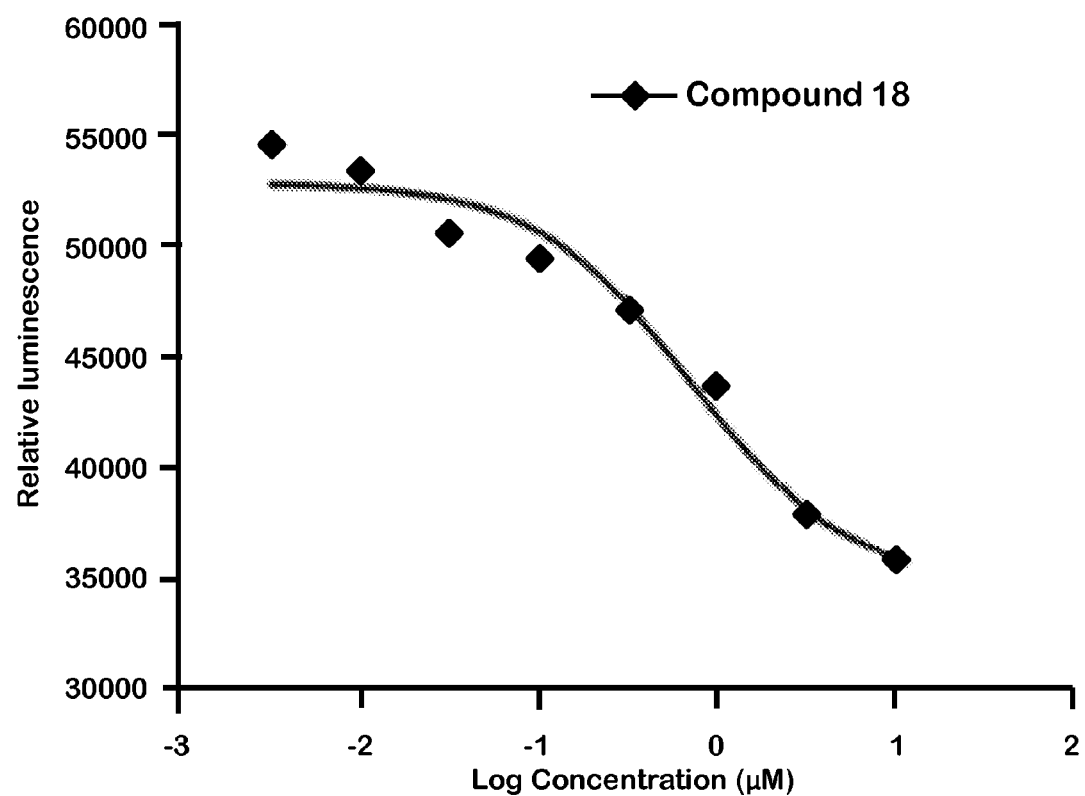
FIG. 4A shows the dose-response curve for HER2:HER3 heterodimer inhibition by Compound 18 in the presence of NRG1.
Figure 4B:
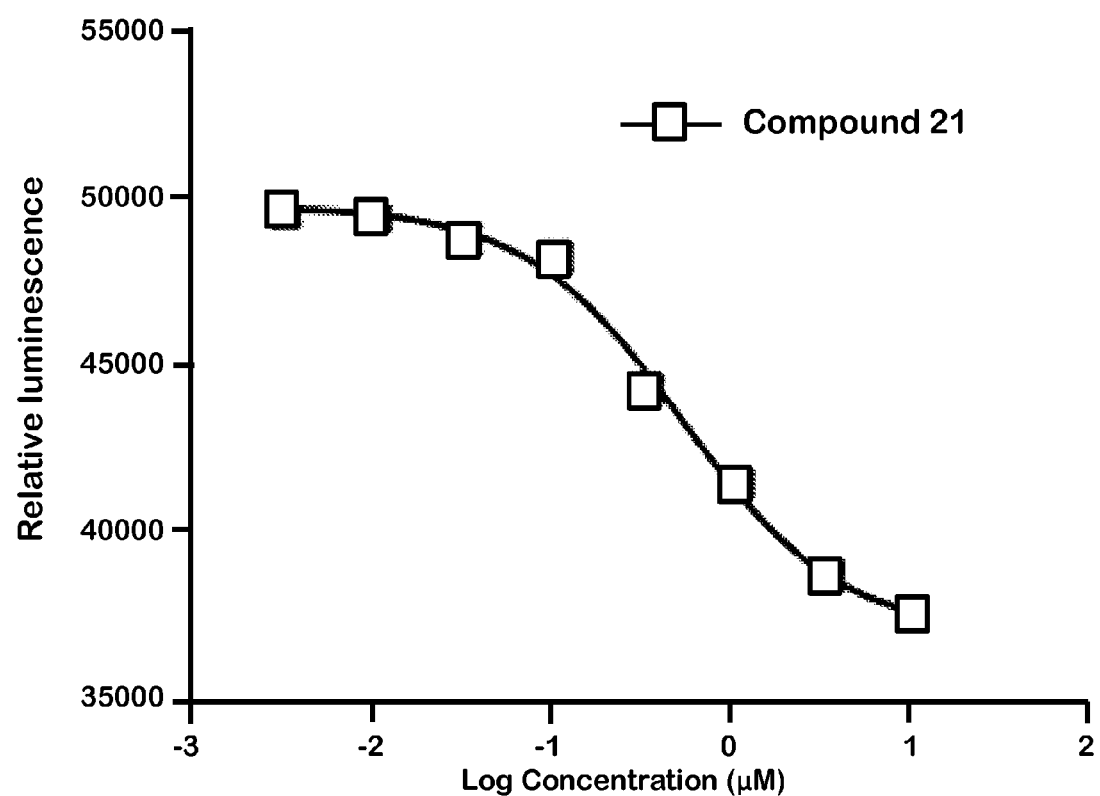
FIG. 4B shows the dose-response curve for HER2:HER3 heterodimer inhibition by Compound 21 in the presence of NRG1.
Figure 4C:
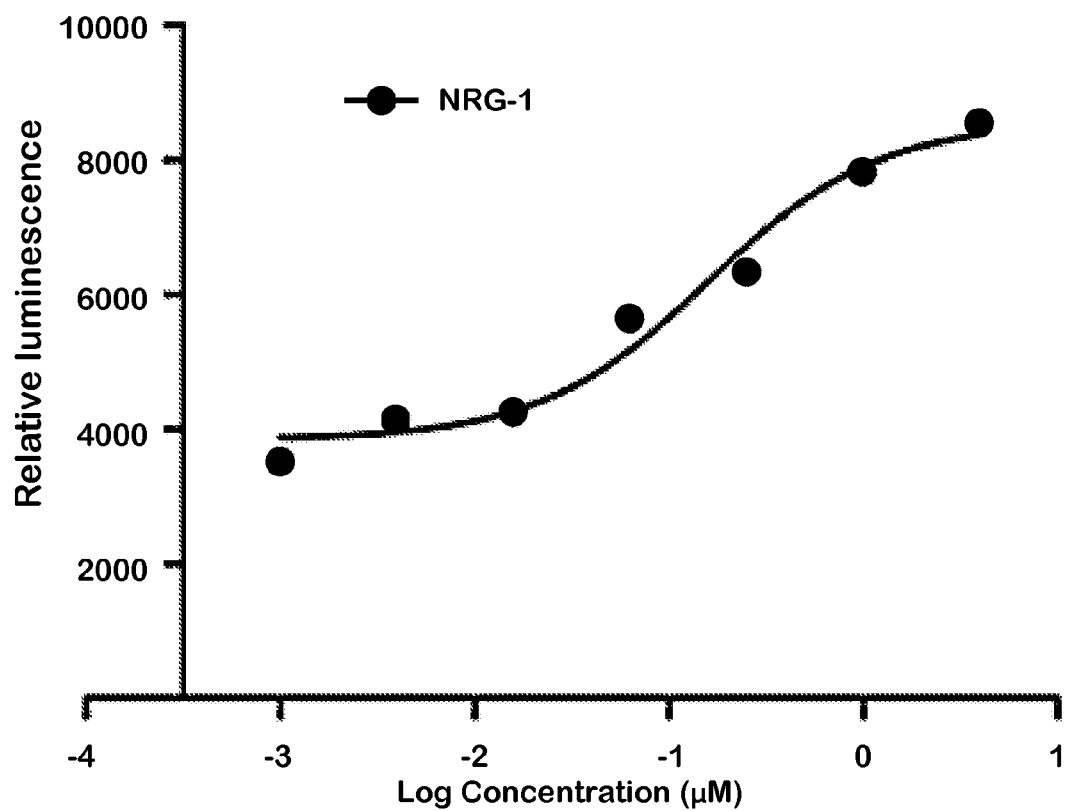
FIG. 4C depicts the dose-response curve for heterodimer formation by Neuregulin-1 (NRG-1).
Figure 4D:
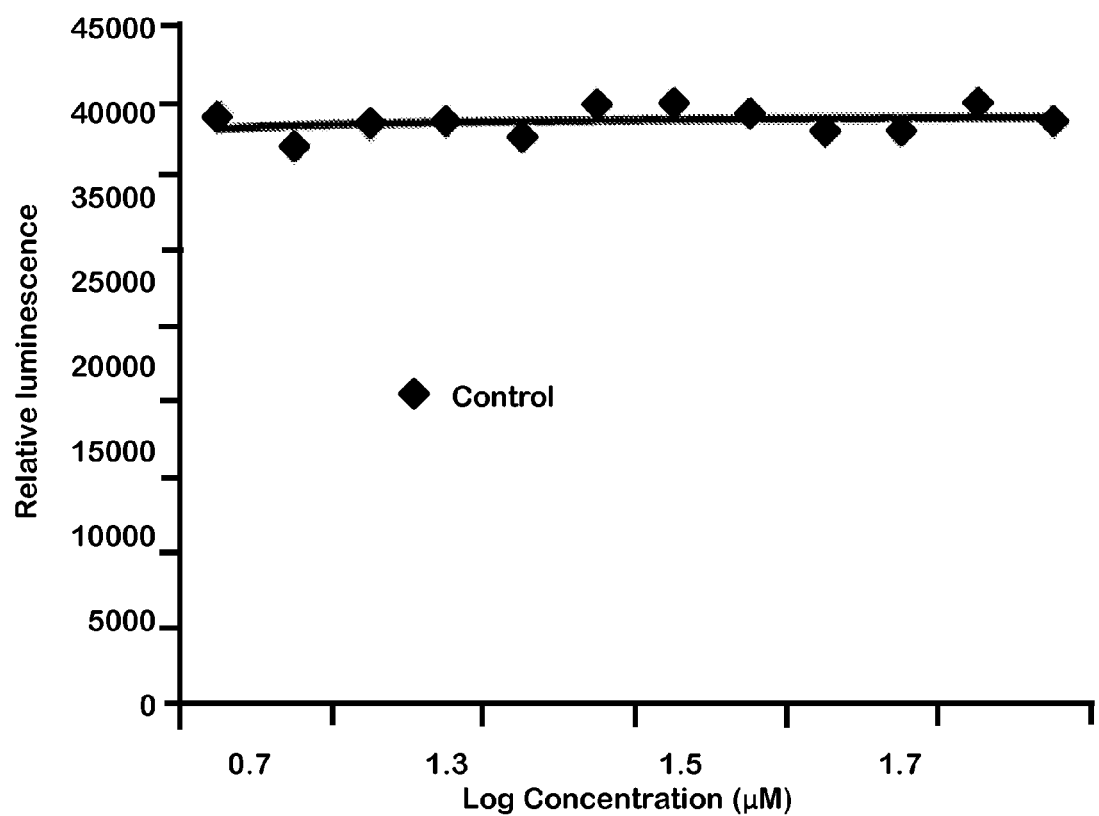
FIG. 4D graphs a dose-response curve for heterodimer formation in the presence of a control compound, for comparison with FIGS. 4A-4C.

HER2-HER3 extracellular domain heterodimerization leads to transphosphorylation of the kinase domain. As shown in FIGS. 4A-4D, Compound 18 inhibited the heterodimerization of HER2-HER3 in a concentration-dependent manner. FIGS. 4A-4D depict the inhibition of heterodimerization in HER2-HER3-transfected U2OS cells by Compound 18 at various concentrations using the PathHunter™ assay (DiscoveRx). FIG. 4A depicts the dose-response curve for heterodimer inhibition by Compound 18 in the presence of 0.3 µM NRG1. FIG. 4B depicts the dose-response curve for heterodimer inhibition by Compound 21. For comparison, FIG. 4C depicts the dose-response curve for heterodimer formation by Neuregulin-1 (NRG-1), a ligand that induces dimerization; and FIG. 4D depicts the effect of a control compound at different concentrations.

Example 6. Western Blot Analysis

Western blot analysis of HER2 protein in BT-474 cells treated with Compound 18 showed that Compound 18 inhibited phosphorylation of the HER2 kinase domain. Controls were total HER2 protein and the kinase inhibitor lapatinib. The results clearly indicated that Compound 18 targeted HER2-overexpressed cells and inhibited the signaling of cell growth by inhibiting PPI between HER2 and HER3. Visualization of glyceraldehyde 3-phosphate dehydrogenase (GAPDH) levels was used to ensure equal sample loading in each lane. Phosphorylation was detected using anti-p-HER2 antibody. Total HER2 protein (T-HER2) was also analyzed.

Inhibition of PPI was also studied in the HER2-overexpressing cancer cell line SKBR-3 with a proximity ligation assay (PLA). This assay uses a fluorescent probe to determine whether two proteins are in close proximity (within about ~16 nm). Red dots seen from the fluorescent probe indicate HER2-HER3 PPI. When Compound 18 was incubated with SKBR-3 cells and visualized with the fluorescent probe, we observed a substantial decrease in red fluorescence dots, indicating that Compound 18 had inhibited HER2-HER3 dimerization.

Figure 5:
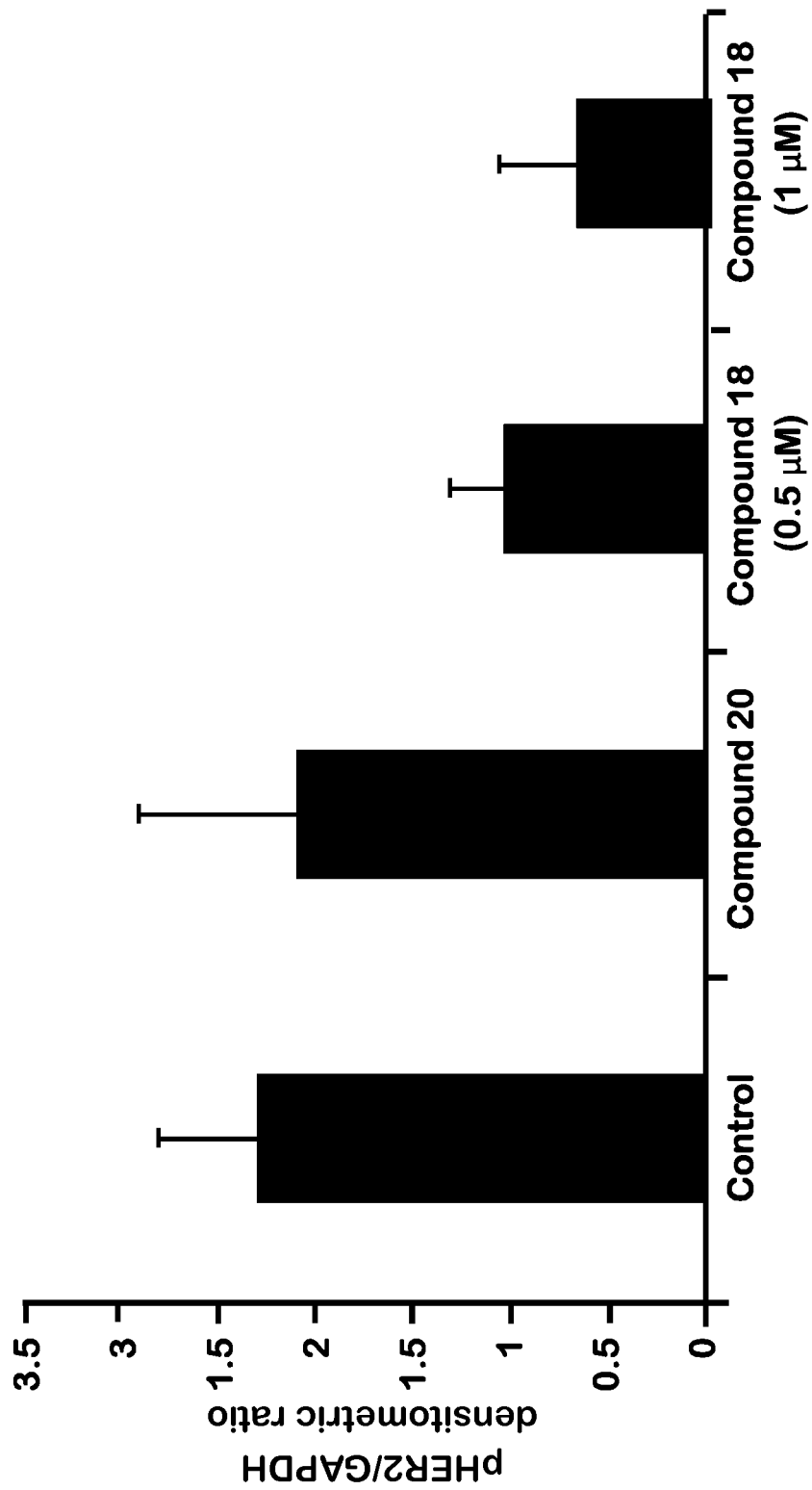
FIG. 5 shows the concentration dependence of the inhibition of phosphorylation of HER2 protein by Compound 18 in Calu-3 lung cancer cells (which overexpress HER2).
Figure 6:
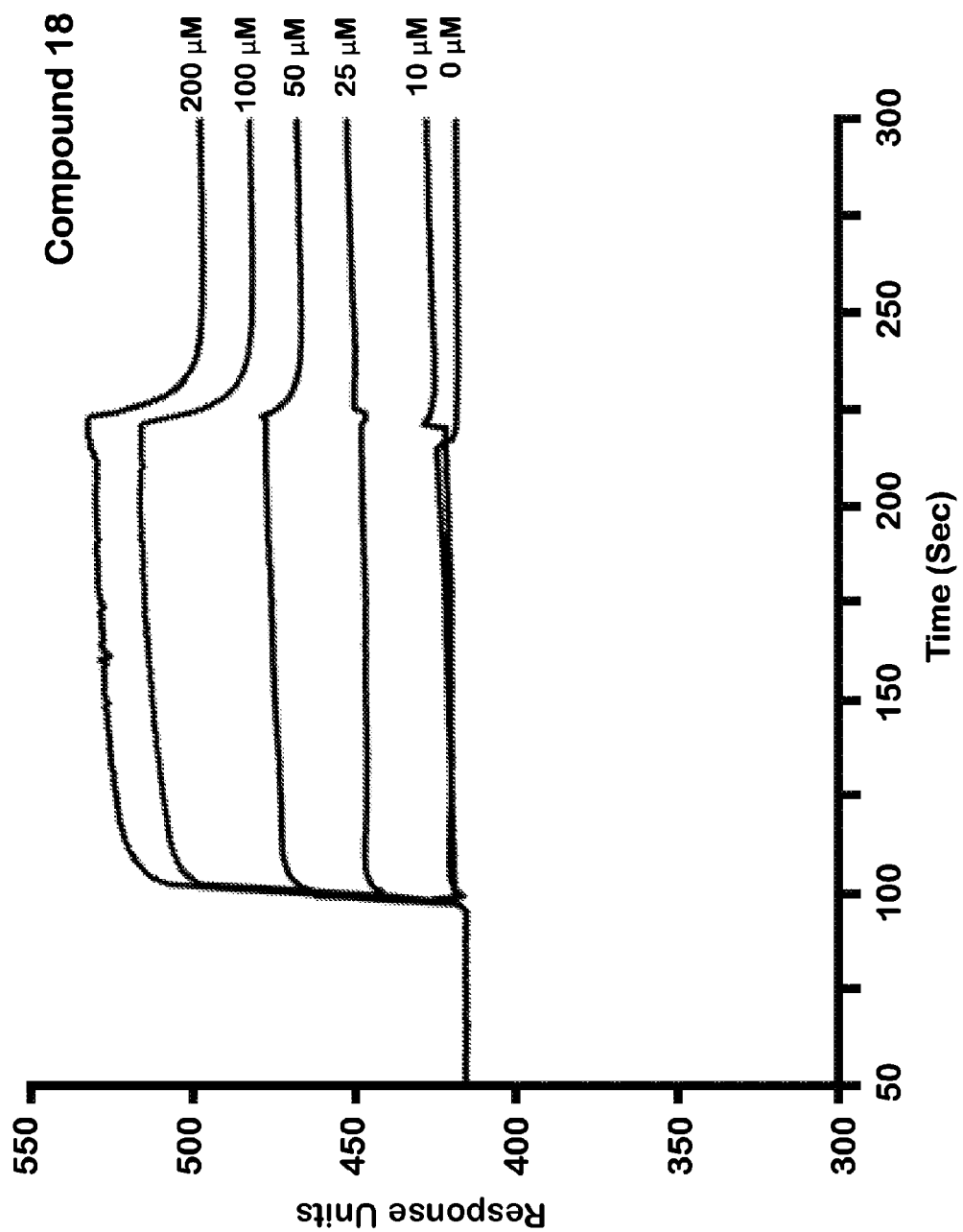
FIG. 6 depicts surface plasmon resonance analysis of the binding of Compound 18 to the HER2 extracellular protein.

We conducted a Western blot analysis of the inhibition of phosphorylated HER2 protein in Calu-3 lung cancer cells lines (which overexpress HER2 protein.) Calu-3 cells were incubated with Compound 18, 20, and control. Results are depicted in FIG. 5. Glyceraldehyde 3-phosphate dehydrogenase (GAPDH) was used to ensure equal sample loading in each lane. Phosphorylation was detected using p-HER2 antibody.

Example 7. Surface Plasmon Resonance Analysis

Figure 7:
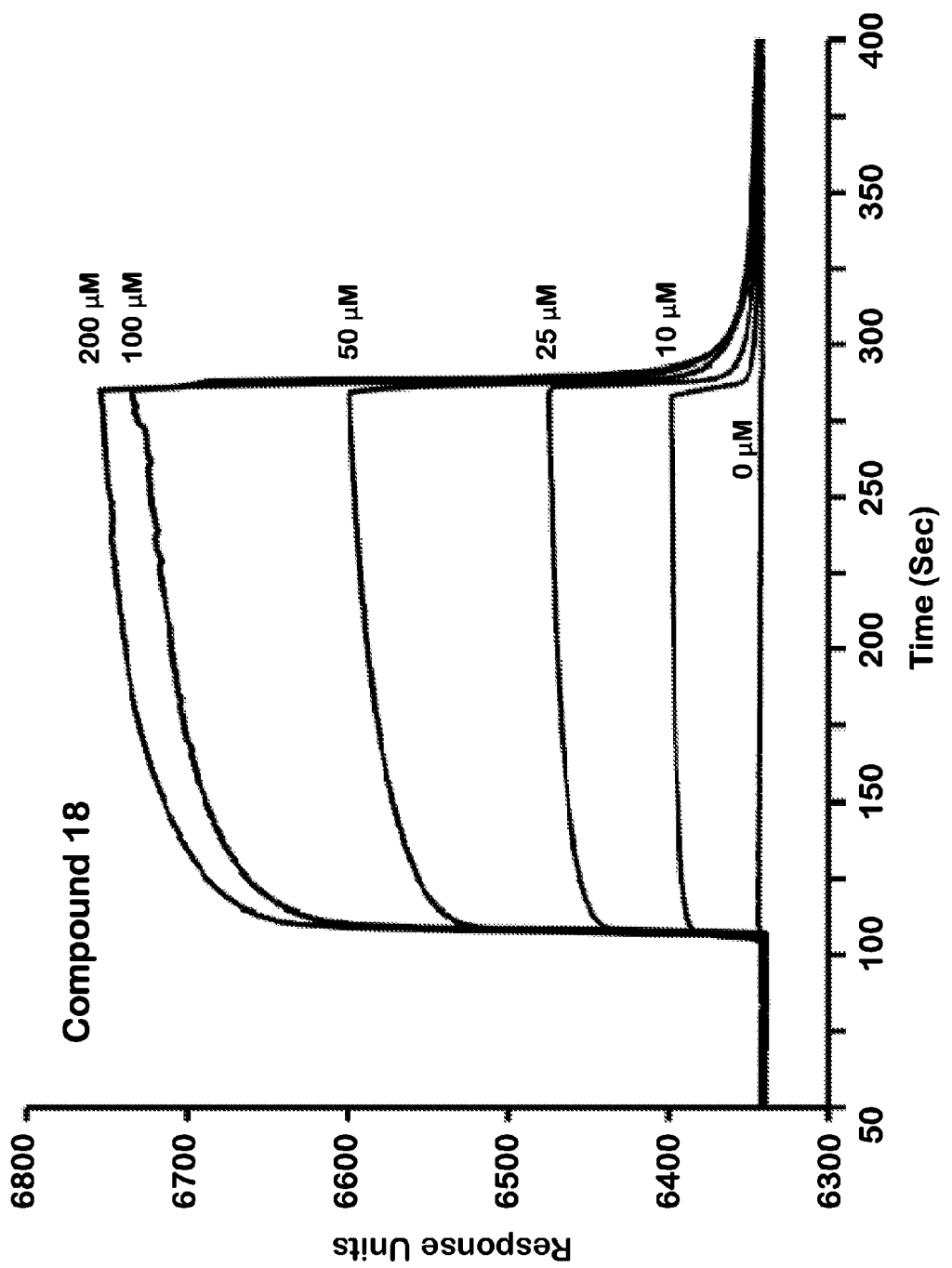
FIG. 7 depicts surface plasmon resonance analysis of the binding of Compound 18 to domain IV of the HER2 protein extracellular domain.
Figure 8:
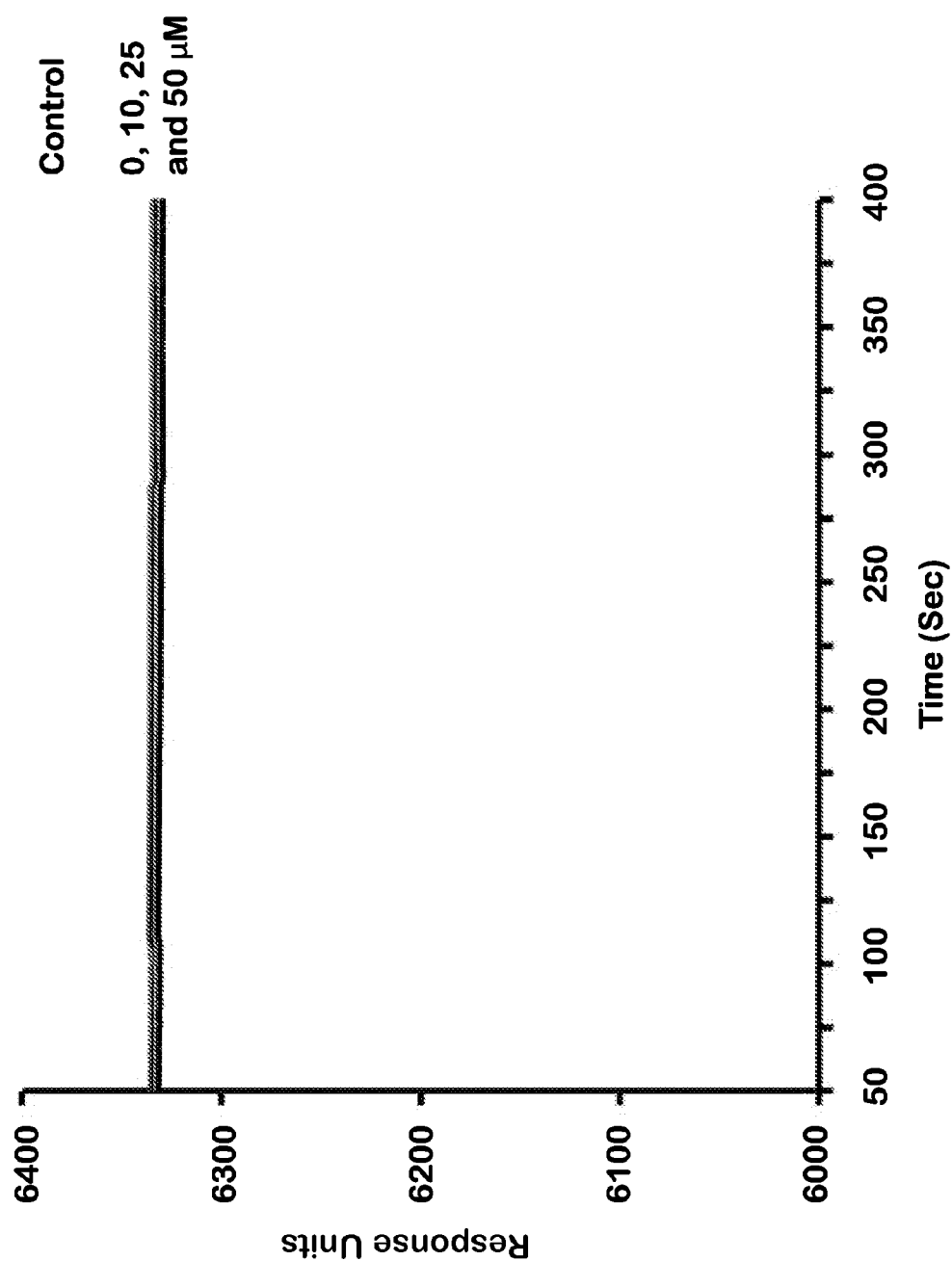
FIG. 8 depicts surface plasmon resonance analysis of a control compound.

We used surface plasmon resonance to analyze the binding of Compound 18 to the HER2 protein extracellular domain. HER2 protein extracellular domain was immobilized, and Compound 18 at various concentrations was used as the analyte. The sensogram depicted in FIG. 7 shows the kinetics of the association and dissociation of Compound 18 to HER2 domain IV protein. FIG. 8 shows similar observations made with a control compound that does not bind to HER2 domain IV.

Example 8. Tumor Growth Analysis

Statistical analysis showed that, as compared to control, Compound 18 significantly decreased tumor volume from days 9-19. Tumors were extracted from the mouse and fixed in formalin. Paraffin-embedded tumor tissue was cut into 5-µm sections, and mounted on slides. PLA was carried out on tumor sections to assess PPI and inhibition. Tumors that had been treated with Compound 18 showed inhibition of HER2:HER3 interaction, as indicated by the absence of red dots compared to the control and lapatinib. HER2 expression level was evaluated in tumor sections using fluorescently-labeled antibody.

Inhibition of HER2-HER3 heterodimers in SKBR-3 cells was determined by PLA. SKBR-3 cells treated with anti-PLA antibodies were used as positive controls. Cells without PLA probes were used as negative controls. Nuclei were stained with DAPI. We observed a decrease in the number of fluorescent red dots in SKBR-3 cells treated with Compound 18 (0.5 and 1 µM), indicating inhibition of dimerization.

Example 9. Tumor Measurements

Figure 9:
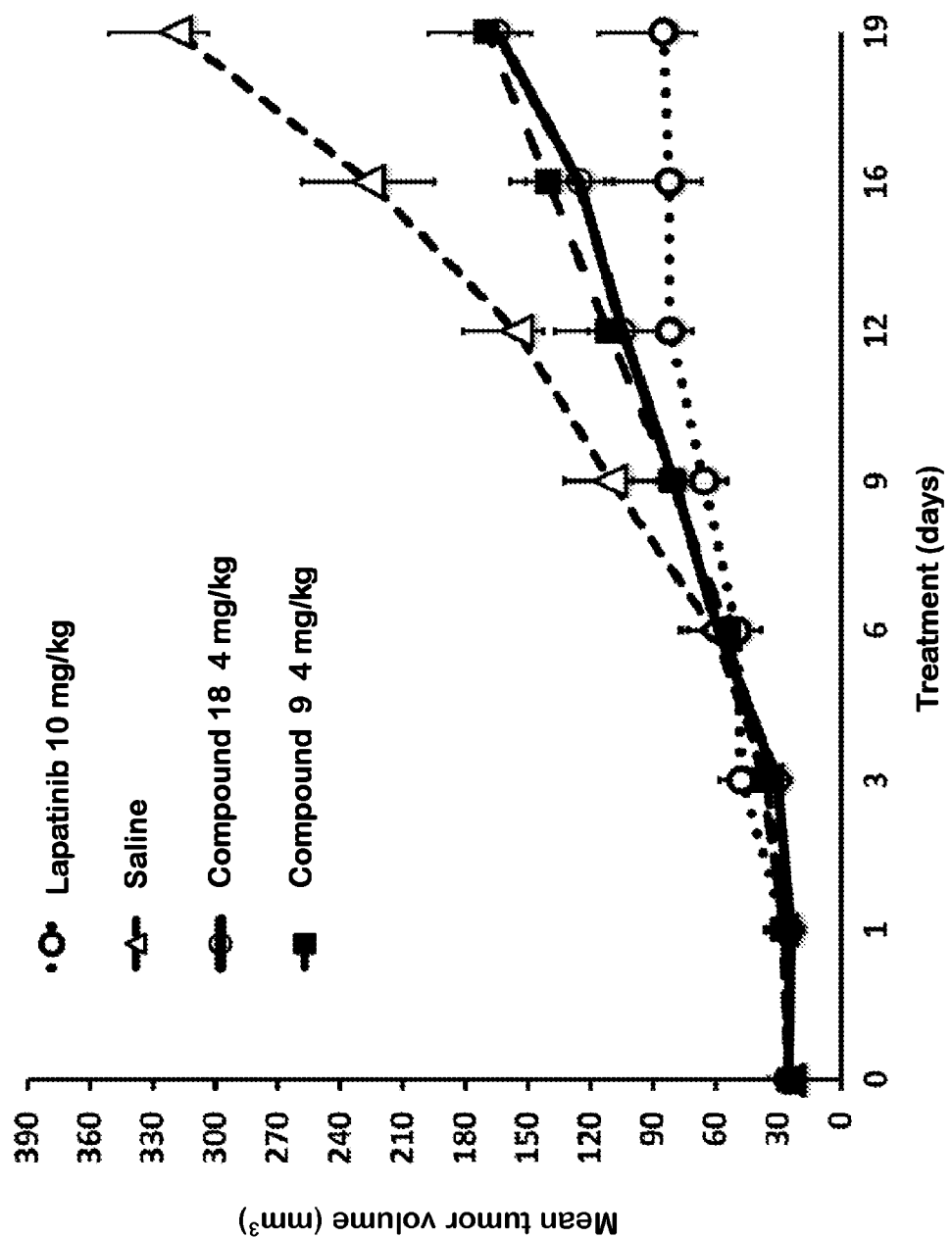
FIG. 9 graphs mean tumor volume as a function of time under various treatments.

We evaluated the ability of Compound 18 to suppress HER2-expressing breast tumors in a xenograft model of breast cancer. Breast cancer tumors were induced in nude mice by injecting 2 million BT-474 cells; these estrogen-dependent cancer cells were stimulated by an implanted estrogen pellet. Compound 9, Compound 18, vehicle, or lapatinib (positive control) were injected just below the tumor at a dose of 4 mg/kg, twice a week for 19 days, for a total of 6 injections. Mice weight and health were monitored daily. Tumor size was measured with Vernier calipers. Tumor volume was estimated using the formula Volume=length×0.5 (width)$^2$. At the end of the experimental period, mice were euthanized and tumor sections were removed and frozen for further analysis. FIG. 9 depicts tumor volume as a function of time for the various treatments. Compound 9, Compound 18, and lapatinib all decreased tumor volume as compared to control, a decrease that was statistically significant from Days 9-19.

Example 10. HER2 Phosphorylation

Western blots were used to assay HER2 phosphorylation in the mouse xenograft breast tumor model, following treatment with Compound 18 or control. We observed that Compound 18 inhibited HER2 phosphorylation as compared to the untreated control group (data not shown).

Example 11. Histology Studies

Histology studies compared organs from mice treated with Compound 18 to organs from untreated control mice. Compound 18 in saline (6 mg/kg) or vehicle was administered to mice i.v. Twenty-four hours after injection the mice were euthanized, organs were harvested, fixed, and prepared on slides. H&E staining of heart, kidneys, lungs, and liver showed histologically normal sections without necrosis, and without infiltration of inflammatory cells such as macrophages. These observations suggest that Compound 18 is not toxic to the organs at the therapeutic dose used in these experiments (although this was not a toxicity study per se).

Example 12. Compound Stability

Figure 10:
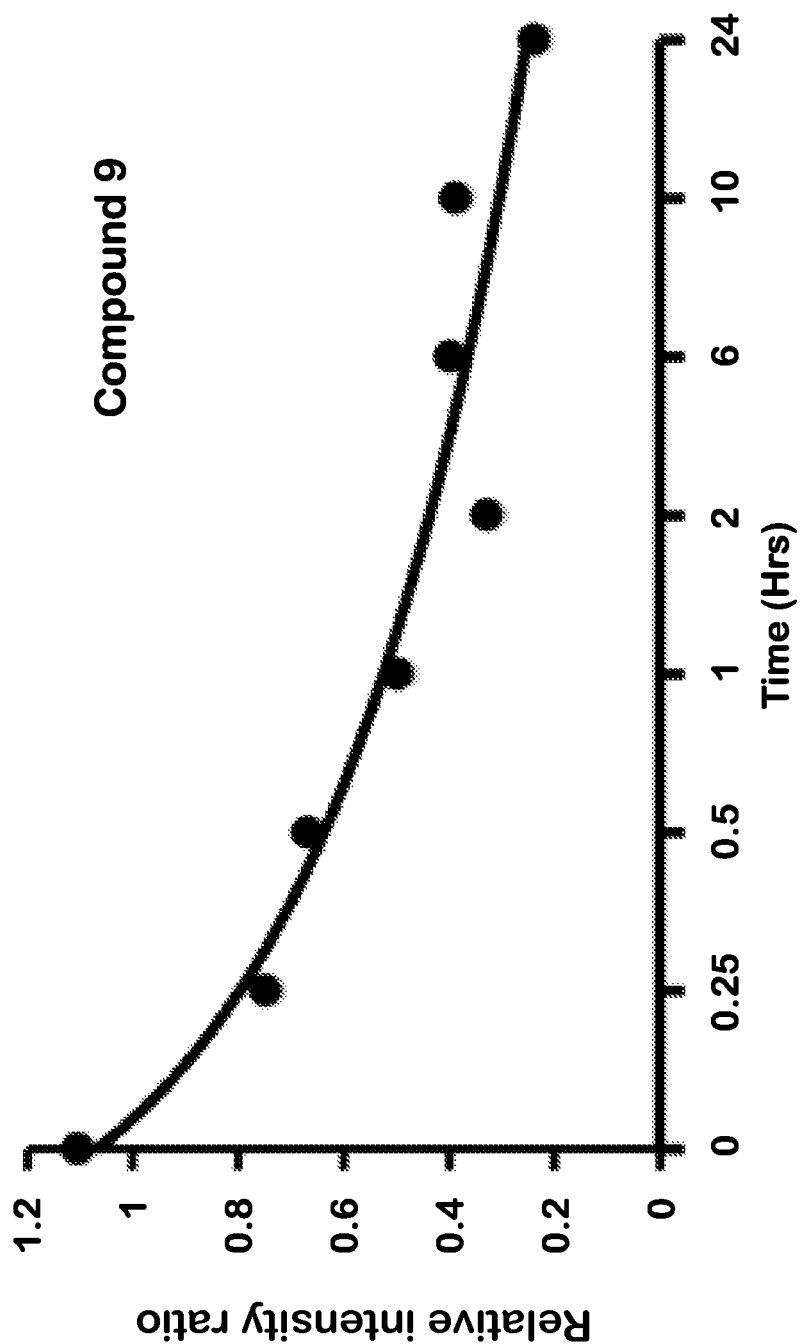
FIG. 10 depicts the degradation of Compound 9 in mouse serum over a period of 24 hours, as measured by electrospray-mass spectrometry.
Figure 11:
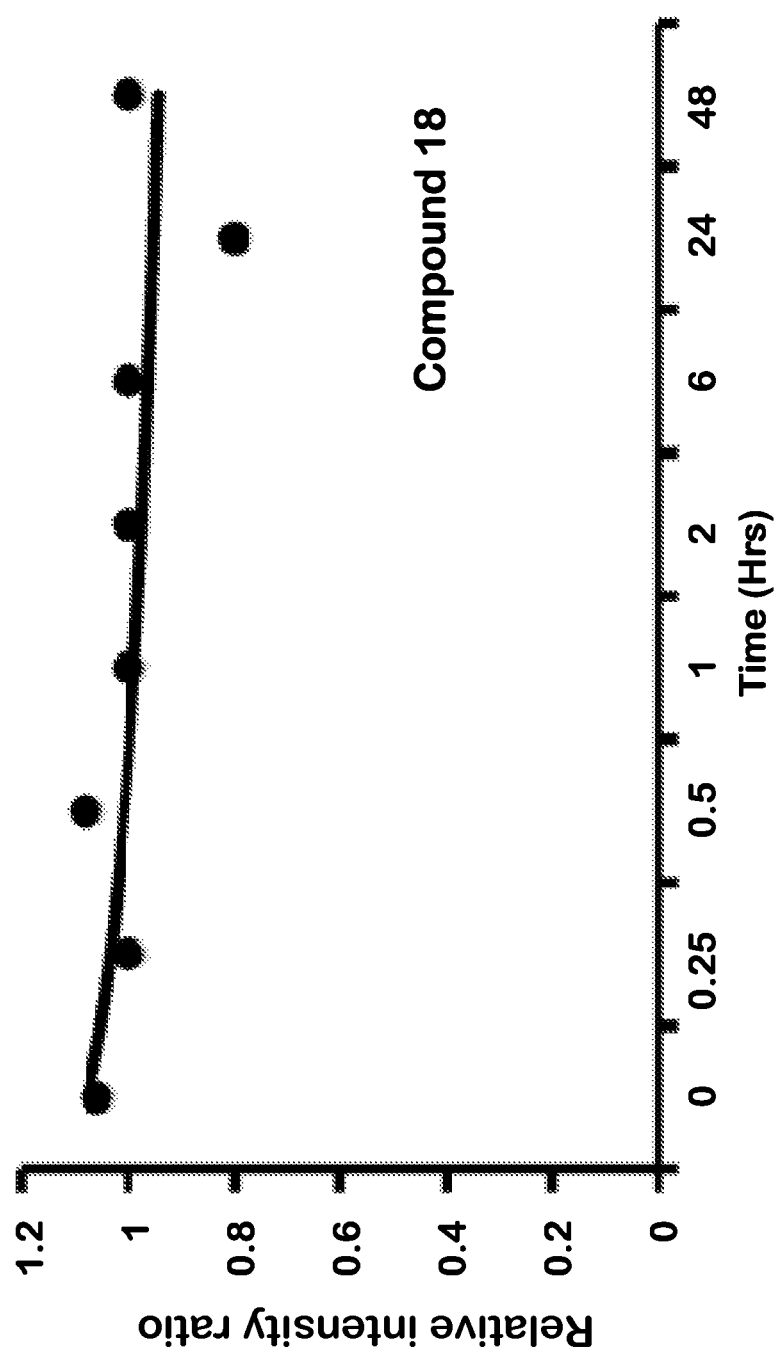
FIG. 11 depicts the stability of Compound 18 in mouse serum over a period of 48 hours, as measured by electrospray-mass spectrometry.

The stabilities of Compound 9 (linear peptidomimetic) and Compound 18 in mouse serum were analyzed. Compounds were incubated in mouse serum for various times, and then extracted using a solid-phase extraction technique. The compounds were analyzed with electrospray-mass spectrometry. A known amount of a freshly-prepared internal standard was used for calibration. FIG. 10 indicates that linear peptidomimetic Compound 9 had been degraded within 24 hours. FIG. 11 shows that, by contrast, Compound 18 was stable after 48 hours in mouse serum.

Example 13. Inhibiting EGFR:HER2 Dimerization

Inhibition of EGFR-HER2 heterodimers in SKBR-3 cells was determined by PLA. SKBR-3 cells treated with anti-PLA antibodies were used as positive controls. Cells without PLA probes were used as negative controls. Nuclei were stained with DAPI. We observed a decrease in the number of fluorescent red dots in SKBR-3 cells treated with Compound 18 (0.5 and 1 µM), indicating inhibition of dimerization (data not shown).

Compound 18 and its stereoisomers also inhibited PPI with EGFR, indicating an intervention that is therapeutically important for many types of cancer. Using Western blot assays, we evaluated Compound 18's ability to inhibit PPI of EGFR and the phosphorylation of the kinase domain of HER2.

A U2OS cell line that had been genetically modified to constitutively express HER2 and HER3 was used to evaluate the inhibition of HER2:HER3 dimerization. Neuregulin 1 was added to the cells to induce HER2:HER3 dimerization, and the cells were then incubated with Compound 18. We tested Compound 18's ability to inhibit neuregulin-1-induced HER2:HER3 dimerization. The effect of Compound 18 on heterodimerization of HER2-HER3 was assayed by monitoring β-galactosidase activity by luminescence. These studies showed that Compound 18 inhibited PPI of EGFR. See FIGS. 4A-4D.

HER2:HER3 heterodimers activate the phosphatidylinositol-3 kinase pathway, even in the presence of tyrosine kinase inhibitors. Thus inhibition by kinase inhibitors alone will not completely inhibit the signaling used in cancer cell growth. Kinase inhibitors target the intracellular target and are then transported across the cell membrane. Compound 18 binds to the extracellular region of the protein, and thus need not cross the cell membrane to be effective.

Example 14. HER2:HER3 Dimerization

The novel compounds inhibit not only EGFR:HER2 dimerization, but also the HER2:HER3 dimerization that predominates in HER2-positive breast cancer. Targeting HER2 has advantages since HER2 is overexpressed in certain types of cancers. HER2-based therapy is effective against both primary and metastatic sites. HER2 activates multiple cell signaling pathways, including phosphatidylinositol-3 kinase and mitogen-activated protein kinase, depending on whether the signaling is from the EGFR:HER2 pathway or the HER2:HER3 pathway. In either case, targeting HER2 extracellular domain is beneficial.

HER2 is the preferred partner in EGFR dimerization, which is stabilized by PPI with domain II and domain IV, which in turn leads to signaling. HER2 overexpression is observed in 30% of breast cancer patients and 18-30% of lung cancer patients, particularly those with non-small cell lung cancer. The coexpression of EGFR and HER2 has been associated with a significantly shortened overall survival rate in lung cancer patients. Thus, a novel therapy that primarily targets EGFR-HER2 and HER2-HER3 dimers rather than the kinase domain provides a valuable new therapy for non-small cell lung cancer, breast cancer, and other cancers overexpressing HER2. The novel compounds can be administered as a sole treatment, or as part of a combination treatment in conjunction with other therapeutic agents such as kinase inhibitors or chemotherapeutic agents known in the art.

To the inventor's knowledge, there have been no prior reports of a cyclic peptidomimetic that targets domain IV of HER2, that inhibits HER2:HER2 dimerization, and that is highly specific for HER2 protein.

Compound 18, its stereoisomers, and the other compounds disclosed herein are potent PPI inhibitors of EGFR dimerization. These compounds are useful in the treatment of HER2-overexpressed cancers, including for example HER2-overexpressed breast, ovarian, and lung cancers.

Example 15. Future Studies

Further in vivo experiments will be conducted to confirm the efficacy of Compound 18 (and other compounds described herein) against tumors. Pharmacokinetics will be observed in a mouse model. Compound 18 (or other disclosed compound) will be injected intravenously into the tail vein of mice. At different time intervals, blood samples will be collected, and the stability of the Compound 18 (or other disclosed compound) will be assessed using LC-MS. Compound 18 (or other disclosed compound) will be fluorescently labeled, and biodistribution of the compound in the body will be evaluated. Primary targets for Compound 18 (or other disclosed compound) are breast and lung cancers. The uptake of Compound 18 (or other disclosed compound) by breast and lung tissue will be evaluated by fluorescence assay and fluorescence microscopy. Compound 18 (or other disclosed compound) will be evaluated in vivo in a transgenic mouse or rat model of HER2-overexpressed breast and lung cancers. Safety pharmacology studies and toxicity studies in animal models will be conducted to estimate the maximum dosage that can be administered without severe side effects.

Although rats are generally preferred for such studies, a mouse model may also be used; either is generally acceptable for determining presumptively safe initial dosages to be tested in Phase I human clinical trials. Dosage transformations from mice to humans are generally based on body surface area. Usually, one-tenth of the LD10 is taken as a safe starting point, and dose escalation is performed according to a modified Fibonacci scheme. Toxicity studies will be conducted in FDA-approved facilities. Toxicity studies include acute (single dose), repeated dose (7, 14, 28, 90 days), genetic toxicology (in vitro/in vivo), specialized studies (inhalation, phototoxicity, arthropathy, allergenicity), and safety pharmacology. Reproductive toxicity will also be examined.

Compound 18 binds domain IV of HER2 protein. Antibodies that bind to HER2 have been reported to exhibit cardiotoxicity. See Sendur M A, Aksoy S, Altundag K. Pertuzumab-induced cardiotoxicity: safety compared with trastuzumab. Future Oncol. 2015 January; 11(1):13; and Adamo V, Ricciardi G R, Adamo B, Ferraro G, Franchina T, Rossello R, Zanghi M, Cicero G, Rizzo S, Caristi N, Russo A. The risk of toxicities from trastuzumab, alone or in combination, in an elderly breast cancer population. Oncology. 2014; 86(1): 16-21. See also Blackwell K L, Burstein H J, Storniolo A M, Rugo H S, Sledge G, Aktan G, Ellis C, Florance A, Vukelja S, Bischoff J, Baselga J, O'Shaughnessy J. Overall survival benefit with lapatinib in combination with trastuzumab for patients with human epidermal growth factor receptor 2-positive metastatic breast cancer: final results from the EGF104900 Study. J Clin Oncol. 2012 Jul. 20; 30(21):2585-92. Compound 18 will therefore also be evaluated to rule out possible cardiotoxicity. Upon completion of these studies, a breast cancer model in non-human primates will be tested, and toxicity will again be assessed.

The animal models provide insight into pharmacological action, pharmacokinetics, dosing, and safety for human patients. Pharmacokinetic studies provide information on the mechanisms of absorption and distribution of the administered drug, the rate at which drug action begins, duration of the effect, chemical changes of the substance in the body (e.g. by enzymes), and the effects and routes of excretion of the metabolites of the drug. In vivo preclinical studies in transgenic animal models for breast and lung cancer are especially helpful since the transgenic animals have diseases similar to those in humans.

The compound(s) will then be tested in human trials in accordance with applicable laws and regulations. The compound(s) will be tested in healthy volunteers at low dosages, followed by Phase II and III clinical trials in HER2-positive breast and lung cancer patients. The administration of most previous anticancer agents has been observed to select for resistance in the tumor cells over time. The compound(s) will therefore also be studied over a period of 6-8 years in humans to evaluate the possible development of resistance.

In case of lung cancer, a powder form for inhalation will be prepared and evaluated, for efficacy in reaching the lung and in inhibiting cancers.

The complete disclosures of all references cited in the specification are hereby incorporated by reference in their entirety, as is the complete disclosure of priority application Ser. No. 61/991,834. Also incorporated by reference are the following publications by the inventors and colleagues: S. Kanthala et al., Structure-activity relationships of peptidomimetics that inhibit PPI of HER2-HER3, *Biopolymers*. 2014 June., vol. 101(6):693-702; and Shanthi Kanthala, S. Banappagari, Gokhale, A., Liu, Y. Y, Xin, G., Zhao, Y. (2014). Novel Peptidomimetics for Inhibition of HER2: HER3 Heterodimerization in HER2-Positive Breast Cancer. Chem. Biol. Drug Des. 2014 Oct. 23. doi: 10.1111/cbdd.12453. [Epub ahead of print]. In the event of an otherwise irresolvable conflict, however, the disclosure of the present specification shall control.

What is claimed:

1. A compound having the structure:

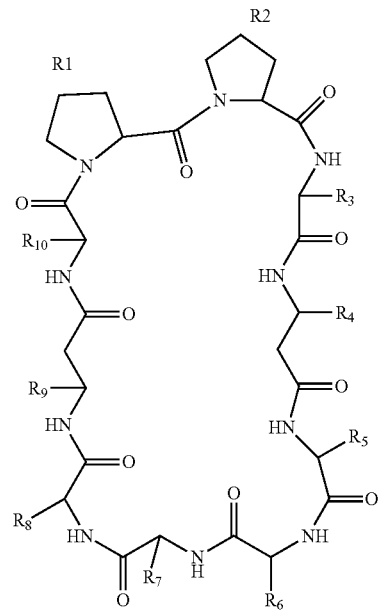

wherein R1, R2, R3, R4, R5, R6, R7, R8, R9, and R10 are each independently selected from the group consisting of $C_1$ to $C_8$ alkyl or substituted alkyl; $C_1$ to $C_8$ alkyl or substituted alkoxy; $C_1$ to $C_8$ alkyl or substituted alkenyl; $C_1$ to $C_{10}$ aryl, heteroaryl, substituted aryl, or substituted heteroaryl; $C_1$ to $C_8$ substituted or unsubstituted amino; amino acid; hydrogen; carboxyl; hydroxyl; or halide; wherein any of R1, R2, R3, R4, R5, R6, R7, R8, R9, and R10 may be the same as or different from any other of R1, R2, R3, R4, R5, R6, R7, R8, R9, and R10; and wherein R1 and R2 are each covalently bonded to any of the carbon atoms of the proline residue to which R1 and R2 are, respectively, shown as being adjacent in the structure depicted;
wherein said compound comprises at least one amino acid residue present primarily in the D-conformation; and wherein said compound comprises at least one chiral center in addition to the D-amino acid residue, and wherein an enantiomeric excess is present at said at least one chiral center.

2. The compound of claim 1, wherein said compound has the following structure

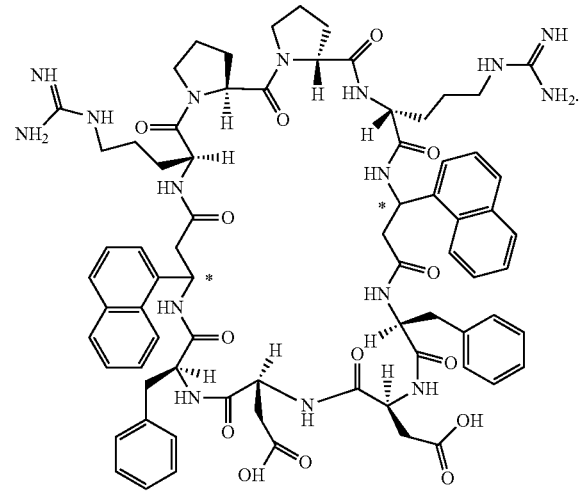

3. The compound of claim 1, wherein said compound has the following structure

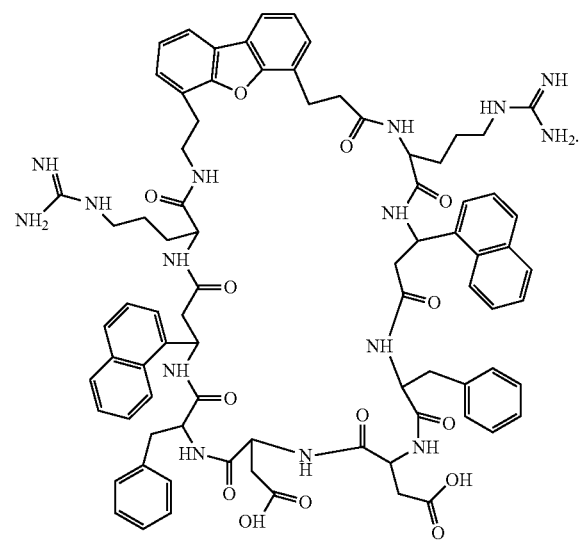 [SMILES: N=C(N)NCCCC1NC(=O)CC(c2cccc3ccccc23)NC(=O)C(Cc2ccccc2)NC(=O)C(CC(=O)O)NC(=O)C(CC(=O)O)NC(=O)C(Cc2ccccc2)NC(=O)CC(c2cccc3ccccc23)NC(=O)C(CCCNC(=N)N)NC(=O)CCc2cccc3c2oc2c(cccc23)CCNC1=O]

4. The compound of claim 1, wherein said compound has the following structure

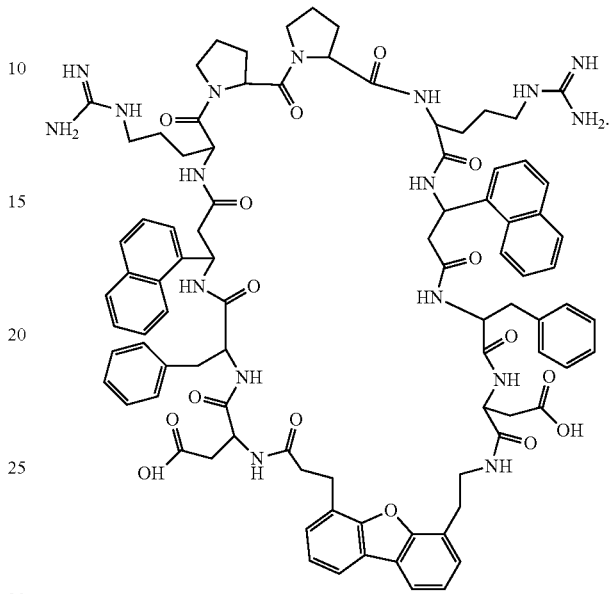

5. The compound of claim 1, wherein said compound comprises at least one Arg-[3-amino-3-(1-napthyl propionic acid)]-Phe-Asp moiety.

6. A method for treating a mammalian patient having a tumor that overexpresses human epidermal growth factor receptor-2, said method comprising administering to the patient or to the tumor an effective amount of the compound of claim 1.

7. A method for treating a mammalian patient having a tumor that overexpresses human epidermal growth factor receptor-2, said method comprising administering to the patient or to the tumor an effective amount of the compound of claim 2.

8. A method for treating a mammalian patient having a tumor that overexpresses human epidermal growth factor receptor-2, said method comprising administering to the patient or to the tumor an effective amount of the compound of claim 3.

9. A method for treating a mammalian patient having a tumor that overexpresses human epidermal growth factor receptor-2, said method comprising administering to the patient or to the tumor an effective amount of the compound of claim 4.

10. A method for treating a mammalian patient having a tumor that overexpresses human epidermal growth factor receptor-2, said method comprising administering to the patient or to the tumor an effective amount of the compound of claim 5.

* * * * *